United States Patent [19]

Vermeulen et al.

[11] Patent Number: 5,670,362
[45] Date of Patent: Sep. 23, 1997

[54] DNA ENCODING AN EIMERIA 100KD ANTIGEN

[75] Inventors: Arnoldus Nicolaas Vermeulen, Cuijk; Paul van den Boogaart, Oss; Jacobus Johannus Kok, Nijmegen, all of Netherlands

[73] Assignee: Akzo Nobel N.V., Arnhem, Netherlands

[21] Appl. No.: 468,853

[22] Filed: Jun. 6, 1995

Related U.S. Application Data

[62] Division of Ser. No. 310,357, Sep. 21, 1994, which is a continuation of Ser. No. 102,865, Aug. 6, 1993, abandoned, which is a continuation of Ser. No. 904,075, Jun. 18, 1992, abandoned.

[30] Foreign Application Priority Data

Jun. 18, 1991 [EP] European Pat. Off. .............. 91201523

[51] Int. Cl.$^6$ .............................. C12N 5/10; C12N 1/21; C12N 15/30; C12N 15/63
[52] U.S. Cl. .................. 435/240.1; 435/69.3; 435/240.2; 435/240.4; 435/252.3; 435/320.1; 536/23.5; 536/23.7
[58] Field of Search .............................. 536/23.5, 23.7; 435/69.3, 252.3, 320.1, 240.1, 240.2, 240.4

[56] References Cited

U.S. PATENT DOCUMENTS

| | | |
|---|---|---|
| 4,554,101 | 11/1985 | Hopp . |
| 4,639,372 | 1/1987 | Murray et al. . |
| 4,710,377 | 12/1987 | Schenkel et al. . |
| 4,874,705 | 10/1989 | Andrews et al. . |
| 4,879,213 | 11/1989 | Fox et al. . |
| 5,028,694 | 7/1991 | Mewman et al. . |
| 5,273,901 | 12/1993 | Jacobson et al. . |
| 5,279,960 | 1/1994 | Anderson et al. . |

FOREIGN PATENT DOCUMENTS

| | | |
|---|---|---|
| 0223710 | 5/1987 | European Pat. Off. . |
| 0328253 | 8/1989 | European Pat. Off. . |
| 0390267 | 10/1990 | European Pat. Off. . |
| WO92/04460 | 3/1992 | WIPO . |

OTHER PUBLICATIONS

C.A. Sutton, *Parasitology*, (1989), 99, 174–187. Great Britain.
H.D. Danforth et al., *The American Society of Parasitologists*, Abstract 30.
J. Ellis et al., *Parasitology Today*, vol. 7, No. 12, 1991, pp. 344–346.
M.C. Jenkins, *Nucleic Acid Research*, vol. 16, No. 20, p. 9863.
C. Monahan et al., *The American Society of Parasitologists*, 84.
M.D. Castle, *J. Parasitol*, 77(3), 1991, pp. 384–390.
M.C. Jenkins et al., *Experimental Parasitology*, 70, pp. 353–362 (1990).
Derwent Abstract No. 89–270713, Jenkins et al. 1989.
Derwent Abstract No. 88–360965, J.B. Dame et al. 1988.
Bowie et al., *Science*, 247:1306 (1990).
Wallach et al., *Infection and Immunity*, 58(2):557–562 (1990).
Kim et al., *Infection and Immunity*, 57(8):2434–2440 (1989).
Stern, *Tibtech*, 9:163–167, 1991.
Berzofsky, *Science*, 229:932–940, 1985.
Jenkins et al., *Mol. and Biochem. Parasitol.*, 25:155–164, 1987.
Young and Davis, *PNAS*, 80:1194–1198, 1983.
Guo et al., *Gene*, 29:251–254, 1984.
Kumar et al., PNAS 87:1337–1341 Feb. 1990.

*Primary Examiner*—Anthony C. Caputa
*Attorney, Agent, or Firm*—Mary E. Gormley

[57] ABSTRACT

The invention is concerned with novel Eimeria proteins with immunogenic properties as well as with DNA sequences encoding these proteins. These proteins can be administered to chickens thereby protecting the chickens against coccidiosis. In addition the DNA encoding these proteins can be used for the preparation of a vector vaccine against coccidiosis.

16 Claims, 10 Drawing Sheets

5,670,362

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
( A ) LENGTH: 1491 base pairs
( B ) TYPE: nucleic acid
( C ) STRANDEDNESS: double
( D ) TOPOLOGY: linear -continued ( i i ) MOLECULE TYPE: cDNA to mRNA ( v ) FRAGMENT TYPE: N-terminal ( v i ) ORIGINAL SOURCE:
    ( A ) ORGANISM: Eimeria acervulina
    ( C ) INDIVIDUAL ISOLATE: Merozoites ( v i i ) IMMEDIATE SOURCE:
    ( A ) LIBRARY: Merozoites cDNA lambda gt11
    ( B ) CLONE: Eam200

( i x ) FEATURE:
    ( A ) NAME/KEY: CDS
    ( B ) LOCATION: 1..1344

( x i ) SEQUENCE DESCRIPTION: SEQ ID NO:1:

```
GAA TTC GGG GGC ACC TCC ACT ACA CAC CTG ACC CGG GAT GAT GCA GTG        48
Glu Phe Gly Gly Thr Ser Thr Thr His Leu Thr Arg Asp Asp Ala Val
 1               5                  10                  15

AAC ACA GCG ATT GAC TCG AAG CTA GAC GAA TTC TGC AAT CCT ACA TCA        96
Asn Thr Ala Ile Asp Ser Lys Leu Asp Glu Phe Cys Asn Pro Thr Ser
            20                  25                  30

GAA CCC CCT GAG GCA TCG GGA AAG GAG GAT TCT GTC GAG GTG GAG GAG       144
Glu Pro Pro Glu Ala Ser Gly Lys Glu Asp Ser Val Glu Val Glu Glu
        35                  40                  45

ACA ACA ACA ACC CCA CCC AGC CGT CCA TTA AGG ATG CAA CAT TTC GTG       192
Thr Thr Thr Thr Pro Pro Ser Arg Pro Leu Arg Met Gln His Phe Val
    50                  55                  60

GAC GAA TTT TGT CTG GAG GAG GCA AAG CGC GCG TGT CAA AAT GGG CTG       240
Asp Glu Phe Cys Leu Glu Glu Ala Lys Arg Ala Cys Gln Asn Gly Leu
65                  70                  75                  80

AGC GCT TAC TGC GAC GCC AGT GTG AGC GCG CGT CAC GAC GTG GGA ACT       288
Ser Ala Tyr Cys Asp Ala Ser Val Ser Ala Arg His Asp Val Gly Thr
                85                  90                  95

GAA CAG CAG CGG ACG AGG GAG TGG CGC TGT TAC GTG GAT GAT TCC CTA       336
Glu Gln Gln Arg Thr Arg Glu Trp Arg Cys Tyr Val Asp Asp Ser Leu
            100                 105                 110

GAC TTC GGC CTC TCC GGC GAT GGT TGT GTA GAC GAC TGT GGG AAT CTC       384
Asp Phe Gly Leu Ser Gly Asp Gly Cys Val Asp Asp Cys Gly Asn Leu
        115                 120                 125

ATC TCG TGC CCT GGT GCG GTA AAC GGC ACC TCC ACT ACA CAC CTG ACC       432
Ile Ser Cys Pro Gly Ala Val Asn Gly Thr Ser Thr Thr His Leu Thr
    130                 135                 140

CGG GAT GAT GCA GTG AAC ACA GCG ATT GAC TCG AAG CTA GAC GAA TTC       480
Arg Asp Asp Ala Val Asn Thr Ala Ile Asp Ser Lys Leu Asp Glu Phe
145                 150                 155                 160

TGC AAT CCT ACA TCA GAA CCC CCT GAG GCA TCG GAG AAG AAG GAA TCC       528
Cys Asn Pro Thr Ser Glu Pro Pro Glu Ala Ser Glu Lys Lys Glu Ser
                165                 170                 175

GTC GAG GTG CCA GAG ACA ACA GCG CTG CCT TCG AAC CCC CCA TCA AAT       576
Val Glu Val Pro Glu Thr Thr Ala Leu Pro Ser Asn Pro Pro Ser Asn
            180                 185                 190

CTA CAA GCT TTG GTG GAT GGG CTT TGT GCT GAG GAG GGG AGA AAA GCG       624
Leu Gln Ala Leu Val Asp Gly Leu Cys Ala Glu Glu Gly Arg Lys Ala
        195                 200                 205

TGC GGA CAA GGG CTG CAA GCC TAC TGC GAC ACT GAT ATG TTC GCA CGC       672
Cys Gly Gln Gly Leu Gln Ala Tyr Cys Asp Thr Asp Met Phe Ala Arg
    210                 215                 220

CAC GAC GTC GGA ACT GGG AGT CAG AGG AAC AGG GAG TGG CGC TGC TAT       720
His Asp Val Gly Thr Gly Ser Gln Arg Asn Arg Glu Trp Arg Cys Tyr
225                 230                 235                 240

GCA CGA GTG TCG TTG GAC TTC GGC ATA TCC GGC GAT GGT TGT GTA GAC       768
Ala Arg Val Ser Leu Asp Phe Gly Ile Ser Gly Asp Gly Cys Val Asp
```

|  |  |  |  |  |  |  |  |  |  |  |  |  |  |  |  |
|--|--|--|--|--|--|--|--|--|--|--|--|--|--|--|--|
|  |  |  | 245 |  |  |  |  | 250 |  |  |  |  | 255 |  |  |
| GAC | TGT | GGG | AAT | CTC | ACA | TCT | TGC | CTT | GGT | GCG | GTA | AAC | GGT | TCC | TCG |
| Asp | Cys | Gly | Asn | Leu | Thr | Ser | Cys | Leu | Gly | Ala | Val | Asn | Gly | Ser | Ser |
|  |  | 260 |  |  |  |  | 265 |  |  |  |  |  | 270 |  |  |

816

ACT ACG CAT CTC TCA CGG GGA GAA CGT ATT CAA AAA CTT ATT GAC ACA    864
Thr Thr His Leu Ser Arg Gly Glu Arg Ile Gln Lys Leu Ile Asp Thr
        275                 280                 285

GAG AAA GCT GGA CGG TGC ACA CCA GAG GAG GGC GAA GAG GCA GGT GGG    912
Glu Lys Ala Gly Arg Cys Thr Pro Glu Glu Gly Glu Glu Ala Gly Gly
        290                 295                 300

AGC CCT GCT CCA GCC CCA GTG CCA GAA CTT CCT GCA GGA GTA CCG GCG    960
Ser Pro Ala Pro Ala Pro Val Pro Glu Leu Pro Ala Gly Val Pro Ala
305                 310                 315                 320

TCT GAG GTG TCG GAC AAG GGC CTG AAG GTT CCT CCA AGG GTC CCA GGT   1008
Ser Glu Val Ser Asp Lys Gly Leu Lys Val Pro Pro Arg Val Pro Gly
                325                 330                 335

GGT GGA GCT TTA CAA GAA ATG GCT GAC GTC AGG TGC ATG GTG TTC TTT   1056
Gly Gly Ala Leu Gln Glu Met Ala Asp Val Arg Cys Met Val Phe Phe
                    340                 345                 350

GCA AAG CAG TGT GTA ACT GAC GAA AGC ATG TGC CAA TAC GCC GTG GCC   1104
Ala Lys Gln Cys Val Thr Asp Glu Ser Met Cys Gln Tyr Ala Val Ala
                355                 360                 365

CGC AAA ATT GAC TCC ACG TGG AAG TGT TAC CCG TAT GGT GCA GTT GAT   1152
Arg Lys Ile Asp Ser Thr Trp Lys Cys Tyr Pro Tyr Gly Ala Val Asp
        370                 375                 380

GAC TCG CAG TCA GGT GAT GCT TGT ACA GAC GAC TGT GGC AAT GCA ATA   1200
Asp Ser Gln Ser Gly Asp Ala Cys Thr Asp Asp Cys Gly Asn Ala Ile
385                 390                 395                 400

AAC TGT CCG GGT ATT CCG AAG AAT GGA GAT GCC GAC GGC ATG AGA ATT   1248
Asn Cys Pro Gly Ile Pro Lys Asn Gly Asp Ala Asp Gly Met Arg Ile
                405                 410                 415

CCA GCC CTC GAT CAC CTG TTC GAA GAG TTG AAG AGC GCC ACC TGC AAG   1296
Pro Ala Leu Asp His Leu Phe Glu Glu Leu Lys Ser Ala Thr Cys Lys
                    420                 425                 430

ATG AGC AAA CAG CAA GAG CTC AAG AAA GTT CAC GTG CAT CGG CAA        1341
Met Ser Lys Gln Gln Glu Leu Lys Lys Val His Val His Arg Gln
                435                 440                 445

TGACGAGAGG                                                          1351

GTGTGCTGAC TGGACGACGT GGGTTGCGAG GCCAAACTCA ATGCTAAGCA AGTGAATGAC  1411

AATATAAGTA TTCTGCTGCC GGAAGTACTG AAGTCTTCCC TTATCCAATG CAAAGCAAGG  1471

CTATCCATGG CCTGGCAGGG                                              1491

( 2 ) INFORMATION FOR SEQ ID NO:2:

( i ) SEQUENCE CHARACTERISTICS:
        ( A ) LENGTH: 447 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

Glu Phe Gly Gly Thr Ser Thr Thr His Leu Thr Arg Asp Asp Ala Val
 1               5                  10                  15

Asn Thr Ala Ile Asp Ser Lys Leu Asp Glu Phe Cys Asn Pro Thr Ser
                20                  25                  30

Glu Pro Pro Glu Ala Ser Gly Lys Glu Asp Ser Val Glu Val Glu Glu
            35                  40                  45

Thr Thr Thr Thr Pro Pro Ser Arg Pro Leu Arg Met Gln His Phe Val

```
           50                      55                      60
Asp  Glu  Phe  Cys  Leu  Glu  Glu  Ala  Lys  Arg  Ala  Cys  Gln  Asn  Gly  Leu
65                       70                      75                       80

Ser  Ala  Tyr  Cys  Asp  Ala  Ser  Val  Ser  Ala  Arg  His  Asp  Val  Gly  Thr
                    85                      90                       95

Glu  Gln  Gln  Arg  Thr  Arg  Glu  Trp  Arg  Cys  Tyr  Val  Asp  Asp  Ser  Leu
               100                     105                     110

Asp  Phe  Gly  Leu  Ser  Gly  Asp  Gly  Cys  Val  Asp  Asp  Cys  Gly  Asn  Leu
          115                     120                     125

Ile  Ser  Cys  Pro  Gly  Ala  Val  Asn  Gly  Thr  Ser  Thr  Thr  His  Leu  Thr
     130                     135                     140

Arg  Asp  Asp  Ala  Val  Asn  Thr  Ala  Ile  Asp  Ser  Lys  Leu  Asp  Glu  Phe
145                     150                     155                     160

Cys  Asn  Pro  Thr  Ser  Glu  Pro  Pro  Glu  Ala  Ser  Glu  Lys  Lys  Glu  Ser
                    165                     170                     175

Val  Glu  Val  Pro  Glu  Thr  Thr  Ala  Leu  Pro  Ser  Asn  Pro  Pro  Ser  Asn
               180                     185                     190

Leu  Gln  Ala  Leu  Val  Asp  Gly  Leu  Cys  Ala  Glu  Glu  Gly  Arg  Lys  Ala
          195                     200                     205

Cys  Gly  Gln  Gly  Leu  Gln  Ala  Tyr  Cys  Asp  Thr  Asp  Met  Phe  Ala  Arg
     210                     215                     220

His  Asp  Val  Gly  Thr  Gly  Ser  Gln  Arg  Asn  Arg  Glu  Trp  Arg  Cys  Tyr
225                     230                     235                     240

Ala  Arg  Val  Ser  Leu  Asp  Phe  Gly  Ile  Ser  Gly  Asp  Gly  Cys  Val  Asp
                    245                     250                     255

Asp  Cys  Gly  Asn  Leu  Thr  Ser  Cys  Leu  Gly  Ala  Val  Asn  Gly  Ser  Ser
               260                     265                     270

Thr  Thr  His  Leu  Ser  Arg  Gly  Glu  Arg  Ile  Gln  Lys  Leu  Ile  Asp  Thr
          275                     280                     285

Glu  Lys  Ala  Gly  Arg  Cys  Thr  Pro  Glu  Glu  Gly  Glu  Ala  Gly  Gly
290                     295                     300

Ser  Pro  Ala  Pro  Ala  Pro  Val  Pro  Glu  Leu  Pro  Ala  Gly  Val  Pro  Ala
305                     310                     315                     320

Ser  Glu  Val  Ser  Asp  Lys  Gly  Leu  Lys  Val  Pro  Pro  Arg  Val  Pro  Gly
                    325                     330                     335

Gly  Gly  Ala  Leu  Gln  Glu  Met  Ala  Asp  Val  Arg  Cys  Met  Val  Phe  Phe
               340                     345                     350

Ala  Lys  Gln  Cys  Val  Thr  Asp  Glu  Ser  Met  Cys  Gln  Tyr  Ala  Val  Ala
          355                     360                     365

Arg  Lys  Ile  Asp  Ser  Thr  Trp  Lys  Cys  Tyr  Pro  Tyr  Gly  Ala  Val  Asp
370                     375                     380

Asp  Ser  Gln  Ser  Gly  Asp  Ala  Cys  Thr  Asp  Cys  Gly  Asn  Ala  Ile
385                     390                     395                     400

Asn  Cys  Pro  Gly  Ile  Pro  Lys  Asn  Gly  Asp  Ala  Asp  Gly  Met  Arg  Ile
                    405                     410                     415

Pro  Ala  Leu  Asp  His  Leu  Phe  Glu  Glu  Leu  Lys  Ser  Ala  Thr  Cys  Lys
               420                     425                     430

Met  Ser  Lys  Gln  Gln  Glu  Leu  Lys  Lys  Val  His  Val  His  Arg  Gln
          435                     440                     445
```

( 2 ) INFORMATION FOR SEQ ID NO:3:

( i ) SEQUENCE CHARACTERISTICS:
        ( A ) LENGTH: 944 base pairs
        ( B ) TYPE: nucleic acid (C) STRANDEDNESS: double
(D) TOPOLOGY: linear (ii) MOLECULE TYPE: cDNA to mRNA (v) FRAGMENT TYPE: N-terminal (vi) ORIGINAL SOURCE:
(A) ORGANISM: Eimeria acervulina (vii) IMMEDIATE SOURCE:
(B) CLONE: Eam45 M1E (ix) FEATURE:
(A) NAME/KEY: CDS
(B) LOCATION: 82..489

(xi) SEQUENCE DESCRIPTION: SEQ ID NO:3:

```
TTTTTTTTT  TTTTGCTCTC  CATTTTCCCA  ACAATATTTC  TCTGTTTCTC  GTCTTAGGTC                               60

CGCCTAACCA  ACATTTAGGA A ATG AGT TCG AAT CCA CGA CTC CGG GAA GCC                                   111
                         Met Ser Ser Asn Pro Arg Leu Arg Glu Ala
                          1           5                      10

TTT GCC CTT TTC GAC AGG GAT GGA GAC GGA GAG TTG ACT GCC AGC GAG                                    159
Phe Ala Leu Phe Asp Arg Asp Gly Asp Gly Glu Leu Thr Ala Ser Glu
             15              20                  25

GCT CTA TTG GCT ATC CGT TCT ACG GGG GTT ATT GTG GCT GCC GAG GAG                                    207
Ala Leu Leu Ala Ile Arg Ser Thr Gly Val Ile Val Ala Ala Glu Glu
         30              35                  40

GCA AGC AGC CTG CCG ACC ACC ATG AAC TGG GAG CAG TTT GAG AGT TGG                                    255
Ala Ser Ser Leu Pro Thr Thr Met Asn Trp Glu Gln Phe Glu Ser Trp
         45              50              55

GTC AAC AAG AAA CTG AGC AGC AGC AAC CCG GAG GCG GAC TTA ATC AAG                                    303
Val Asn Lys Lys Leu Ser Ser Ser Asn Pro Glu Ala Asp Leu Ile Lys
     60              65                  70

TCC TTT AAA GTA TTT GAC ACA AAG GGG GAC GGC ACT CTC TCG ACA GAC                                    351
Ser Phe Lys Val Phe Asp Thr Lys Gly Asp Gly Thr Leu Ser Thr Asp
 75              80              85                  90

GAA CTT ATG CAA GTT ATA AAG ACC TTA GGA GAT CTG CTG ACG GAC GAA                                    399
Glu Leu Met Gln Val Ile Lys Thr Leu Gly Asp Leu Leu Thr Asp Glu
             95                  100                 105

GAG GTT GAG CGT ATG GTT AAT GAC GCA GAC CCA AGC AAA ACA GGG CGA                                    447
Glu Val Glu Arg Met Val Asn Asp Ala Asp Pro Ser Lys Thr Gly Arg
             110                 115                 120

ATT AAA TAT GCC GAT TTT GTA AAG TAC CTC TTG AGC AAC TGACTTCATG                                     496
Ile Lys Tyr Ala Asp Phe Val Lys Tyr Leu Leu Ser Asn
             125                 130                 135

GGTTCATGCA GCACCCCACC ACAGCAGTTA AAGCGCTCCT GCTATACTCA CGTACATGTT                                  556

GTTCGTGAAC GTATGCATGG CTAGGGTTAT TTGAACCGCA CGGGTTCATT TTGTGCGTTT                                  616

AGTGGAGCCT CTGCCCATCG GGTGCTTCCT CACCTAGCTC TCACAGCAGA GGGCCGAGCG                                  676

CAGGTGTTGC TTTGCCATGG TGCATGTGGG AGTTGCAATC TTTAACCTGC GTGCCGCCTG                                  736

TGTGTTGCTC GCTGCACAGC TGGGGCAGTA TTGCATGCAC CACATGCATT ACGATGGACA                                  796

AAAGACGGGG AGGGGAGCTA TGCCTTTCGG TGCTTCTGCC GAGAAAGCGA GCAGCATGCA                                  856

TGCATGTGTG CAACATACAT GCGCCAATGT GAGCTATACA ACCCCTCCAG GCCTTTTTA                                   916

TGTGAACGAT TTGGAACCGA CAAGTCAG                                                                     944
```

(2) INFORMATION FOR SEQ ID NO:4:

(i) SEQUENCE CHARACTERISTICS:
(A) LENGTH: 135 amino acids
(B) TYPE: amino acid
(D) TOPOLOGY: linear ( i i ) MOLECULE TYPE: protein ( x i ) SEQUENCE DESCRIPTION: SEQ ID NO:4:

| Met | Ser | Ser | Asn | Pro | Arg | Leu | Arg | Glu | Ala | Phe | Ala | Leu | Phe | Asp | Arg |
|---|---|---|---|---|---|---|---|---|---|---|---|---|---|---|---|
| 1 | | | | 5 | | | | 10 | | | | | | 15 | |

| Asp | Gly | Asp | Gly | Glu | Leu | Thr | Ala | Ser | Glu | Ala | Leu | Leu | Ala | Ile | Arg |
|---|---|---|---|---|---|---|---|---|---|---|---|---|---|---|---|
| | | | 20 | | | | | 25 | | | | | 30 | | |

| Ser | Thr | Gly | Val | Ile | Val | Ala | Ala | Glu | Glu | Ala | Ser | Ser | Leu | Pro | Thr |
|---|---|---|---|---|---|---|---|---|---|---|---|---|---|---|---|
| | | 35 | | | | | 40 | | | | | 45 | | | |

| Thr | Met | Asn | Trp | Glu | Gln | Phe | Glu | Ser | Trp | Val | Asn | Lys | Lys | Leu | Ser |
|---|---|---|---|---|---|---|---|---|---|---|---|---|---|---|---|
| | 50 | | | | | 55 | | | | | 60 | | | | |

| Ser | Ser | Asn | Pro | Glu | Ala | Asp | Leu | Ile | Lys | Ser | Phe | Lys | Val | Phe | Asp |
|---|---|---|---|---|---|---|---|---|---|---|---|---|---|---|---|
| 65 | | | | | 70 | | | | 75 | | | | | 80 | |

| Thr | Lys | Gly | Asp | Gly | Thr | Leu | Ser | Thr | Asp | Glu | Leu | Met | Gln | Val | Ile |
|---|---|---|---|---|---|---|---|---|---|---|---|---|---|---|---|
| | | | | 85 | | | | | 90 | | | | | 95 | |

| Lys | Thr | Leu | Gly | Asp | Leu | Leu | Thr | Asp | Glu | Glu | Val | Glu | Arg | Met | Val |
|---|---|---|---|---|---|---|---|---|---|---|---|---|---|---|---|
| | | | 100 | | | | | 105 | | | | | 110 | | |

| Asn | Asp | Ala | Asp | Pro | Ser | Lys | Thr | Gly | Arg | Ile | Lys | Tyr | Ala | Asp | Phe |
|---|---|---|---|---|---|---|---|---|---|---|---|---|---|---|---|
| | | 115 | | | | | 120 | | | | | 125 | | | |

| Val | Lys | Tyr | Leu | Leu | Ser | Asn |
|---|---|---|---|---|---|---|
| | 130 | | | | | 135 |

( 2 ) INFORMATION FOR SEQ ID NO:5:

( i ) SEQUENCE CHARACTERISTICS:
        ( A ) LENGTH: 1631 base pairs
        ( B ) TYPE: nucleic acid
        ( C ) STRANDEDNESS: double
        ( D ) TOPOLOGY: linear ( i i ) MOLECULE TYPE: cDNA to mRNA ( v i i ) IMMEDIATE SOURCE:
        ( B ) CLONE: Eam45 M3E ( i x ) FEATURE:
        ( A ) NAME/KEY: CDS
        ( B ) LOCATION: 505..1494

( x i ) SEQUENCE DESCRIPTION: SEQ ID NO:5:

```
CAACACATTT GGGGGAGCTC AGCTAAAGTA TTTGTCGTTT CAGCCACAAG GCCAACTCCC      60

TCTTCCTCAG GGACCAAAAT CAGCTGTGAT GAAGCCCTCA GCGAGTGGAA GACAGGGTTT     120

GCAAATTTCG AGGGCCAAGA TCCTCCGGCA TACTCAGACG CCACCTTGGT ATATGCAAAC     180

CCAAATTCGG TAGGCCTTGT CAGCCTGCTG AGCGCGACGC AGCAGACCAT TTACTGCGGA     240

ACTACAGATA CGTGTGGAGA TGATACCCTC GTTTGCTACT ACAAGCCCTC TGGCATAGAG     300

GAGGAAACGG TTCCTGTGAG CGAAGATCTG TGGCACAAGT TGCAGGAATC CACAAGGTG     360

AAGCCCGCAC TGGCAGCTGA CGATGCGGGC TCCCTAGCTG CGTGACAGCA GTCAATGCTG     420

CTCGGGGTGC CGGAGTCTGG AACTTGCGGG CTTCACAAAA GGCTCTAACT TGGAGGCTGG     480

CGCAAAGAAG CTGTATGGAT TGAC ATG CGA ACG ATA GAT ACC ATG ACA GTC       531
              Met Arg Thr Ile Asp Thr Met Thr Val
               1               5

GAC CCA ACG GCG GCA CGA GGC CAC ACT ATC ATC TAC GCC ACA AAA GAA     579
Asp Pro Thr Ala Ala Arg Gly His Thr Ile Ile Tyr Ala Thr Lys Glu
10              15              20              25

GGG GAC ACT CCT CCA ACG GCA GAA GAA GCC GTT GAG CAA TGG AAA AAA     627
Gly Asp Thr Pro Pro Thr Ala Glu Glu Ala Val Glu Gln Trp Lys Lys
        30              35              40
```

-continued

| | | | | | | | | | | | | | | | | |
|---|---|---|---|---|---|---|---|---|---|---|---|---|---|---|---|---|
| GGG | GCA | GCA | CGG | CTC | GGC | ACC | GGC | GTC | CTG | CCT | GCC | TTC | ACG | AAG | AAG | 675 |
| Gly | Ala | Ala | Arg<br>45 | Leu | Gly | Thr | Gly | Val<br>50 | Leu | Pro | Ala | Phe | Thr<br>55 | Lys | Lys | |
| TCG | AAA | GCA | GCC | GAC | GGC | GAG | ATC | TAC | TAT | GAC | AGC | GCA | GTA | GCC | GGT | 723 |
| Ser | Lys<br>60 | Ala | Ala | Asp | Gly | Glu<br>65 | Ile | Tyr | Tyr | Asp | Ser<br>70 | Ala | Val | Ala | Gly | |
| TTC | GTC | TCC | ATT | ATG | ACT | GAT | AAT | ACC | CGC | GAA | ACG | GCA | TGC | TAC | AAA | 771 |
| Phe | Val<br>75 | Ser | Ile | Met | Thr | Asp<br>80 | Asn | Thr | Arg | Glu | Thr<br>85 | Ala | Cys | Tyr | Lys | |
| GCT | ACA | GGT | TGC | ACT | AAC | GCC | GCA | CTC | ATC | TGC | TTA | CTT | AAA | GGG | CCA | 819 |
| Ala<br>90 | Thr | Gly | Cys | Thr | Asn<br>95 | Ala | Ala | Leu | Ile | Cys<br>100 | Leu | Leu | Lys | Gly | Pro<br>105 | |
| ACT | CTG | GAG | GAA | AAC | CAA | AAG | CCC | ATC | ACC | GAC | GAA | ACA | TGG | AAA | AAG | 867 |
| Thr | Leu | Glu | Glu | Asn<br>110 | Gln | Lys | Pro | Ile | Thr<br>115 | Asp | Glu | Thr | Trp | Lys<br>120 | Lys | |
| GTC | TTG | GAT | GTC | TAC | GGA | GAA | AAG | ATG | GAT | TTC | AAA | GAA | CGT | GAG | GAG | 915 |
| Val | Leu | Asp | Val<br>125 | Tyr | Gly | Glu | Lys | Met<br>130 | Asp | Phe | Lys | Glu | Arg<br>135 | Glu | Glu | |
| GGA | GAA | AGC | TGC | CTC | ACG | GAG | ATA | AAT | GAT | TTC | CGC | GCC | CAA | GAT | GGC | 963 |
| Gly | Glu | Ser<br>140 | Cys | Leu | Thr | Glu | Ile<br>145 | Asn | Asp | Phe | Arg | Ala<br>150 | Gln | Asp | Gly | |
| CTC | GCT | CTG | CCA | CCG | TTC | GCT | GCC | GCG | ACG | GAC | TTA | CAT | GGT | GCG | AAA | 1011 |
| Leu | Ala<br>155 | Leu | Pro | Pro | Phe | Ala<br>160 | Ala | Ala | Thr | Asp | Leu<br>165 | His | Gly | Ala | Lys | |
| CCG | AAG | GCT | TCC | GAA | TTG | ATT | GGG | AAA | GGC | TTG | ACG | TGC | GAG | GCC | CTC | 1059 |
| Pro<br>170 | Lys | Ala | Ser | Glu | Leu<br>175 | Ile | Gly | Lys | Gly | Leu<br>180 | Thr | Cys | Glu | Ala | Leu<br>185 | |
| AAG | TCT | GGG | AAT | GCC | CCC | ATC | TTG | TTT | ACC | GAC | CAA | GAA | ATA | AGC | CTG | 1107 |
| Lys | Ser | Gly | Asn | Ala<br>190 | Pro | Ile | Leu | Phe | Thr<br>195 | Asp | Gln | Glu | Ile | Ser<br>200 | Leu | |
| ATG | TAC | TAC | ATG | GGT | GAA | ACT | GCC | ACT | TGC | TCT | TTA | GCC | GTC | AGA | GAA | 1155 |
| Met | Tyr | Tyr | Met<br>205 | Gly | Glu | Thr | Ala | Thr<br>210 | Cys | Ser | Leu | Ala | Val<br>215 | Arg | Glu | |
| TGG | AAA | AAT | GGC | ATT | GAC | TTG | TTC | AGC | GAC | TTC | ACC | ATC | CCT | CCA | AAG | 1203 |
| Trp | Lys | Asn<br>220 | Gly | Ile | Asp | Leu | Phe<br>225 | Ser | Asp | Phe | Thr | Ile<br>230 | Pro | Pro | Lys | |
| TAC | ACT | TCA | ACC | GAA | GAA | GTT | TAC | AAG | AAG | GGA | GCA | GCA | ACA | AAC | TTT | 1251 |
| Tyr | Thr<br>235 | Ser | Thr | Glu | Glu | Val<br>240 | Tyr | Lys | Lys | Gly | Ala<br>245 | Ala | Thr | Asn | Phe | |
| ATC | TCC | CTC | GTC | AGC | GAA | GGA | ACT | GAT | ACC | AAA | ATA | AAA | TGC | TAC | ACC | 1299 |
| Ile | Ser | Leu | Val<br>250 | Ser | Glu | Gly<br>255 | Thr | Asp | Thr | Lys<br>260 | Ile | Lys | Cys | Tyr | Thr<br>265 | |
| GTG | ACA | GGC | TGC | AGC | GAA | CCA | GGA | TTG | CTT | TGC | CTG | CTG | CAA | CCT | CCT | 1347 |
| Val | Thr | Gly | Cys | Ser<br>270 | Glu | Pro | Gly | Leu | Leu<br>275 | Cys | Leu | Leu | Gln | Pro<br>280 | Pro | |
| GTC | TTC | AAG | GAG | AAC | GAA | GCA | CCC | ATC | AGC | GAG | GAA | ACC | TGG | AAA | AAG | 1395 |
| Val | Phe | Lys | Glu<br>285 | Asn | Glu | Ala | Pro | Ile<br>290 | Ser | Glu | Glu | Thr | Trp<br>295 | Lys | Lys | |
| GTT | ACA | GAC | ACC | GTC | ACT | AGT | GGA | GCT | GCC | TCT | GCC | TCT | GCT | TAT | GGA | 1443 |
| Val | Thr | Asp<br>300 | Thr | Val | Thr | Ser<br>305 | Gly | Ala | Ala | Ser<br>310 | Ala | Ser | Ala | Tyr | Gly | |
| GCC | CTC | CTG | AGC | AGC | GTT | TTC | GTT | GCT | GTC | GGT | CTT | TTC | GCG | CTC | AGC | 1491 |
| Ala | Leu<br>315 | Leu | Ser | Ser | Val | Phe<br>320 | Val | Ala | Val | Gly<br>325 | Leu | Phe | Ala | Leu | Ser | |
| TTC<br>Phe<br>330 | TAAGCGCACA | CAGCTCTCCT | GCAGCACTTG | AGTGGCAGTG | CAATGCTTCT | | | | | | | | | | | 1544 |

CTGCCACTCT ATCCCACATC GCAGTAATTC AGGCAGCGCA TTAATTCCAT CAAACTCTTT  1604

TCATTGAGAA GAAGCGCTTA ATACTCT  1631

( 2 ) INFORMATION FOR SEQ ID NO:6:

( i ) SEQUENCE CHARACTERISTICS:
        ( A ) LENGTH: 330 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| Met | Arg | Thr | Ile | Asp | Thr | Met | Thr | Val | Asp | Pro | Thr | Ala | Ala | Arg | Gly |
|---|---|---|---|---|---|---|---|---|---|---|---|---|---|---|---|
| 1 | | | | 5 | | | | | 10 | | | | | 15 | |
| His | Thr | Ile | Ile | Tyr | Ala | Thr | Lys | Glu | Gly | Asp | Thr | Pro | Pro | Thr | Ala |
| | | | 20 | | | | | 25 | | | | | 30 | | |
| Glu | Glu | Ala | Val | Glu | Gln | Trp | Lys | Lys | Gly | Ala | Ala | Arg | Leu | Gly | Thr |
| | | 35 | | | | | 40 | | | | | 45 | | | |
| Gly | Val | Leu | Pro | Ala | Phe | Thr | Lys | Lys | Ser | Lys | Ala | Ala | Asp | Gly | Glu |
| | 50 | | | | | 55 | | | | | 60 | | | | |
| Ile | Tyr | Tyr | Asp | Ser | Ala | Val | Ala | Gly | Phe | Val | Ser | Ile | Met | Thr | Asp |
| 65 | | | | | 70 | | | | | 75 | | | | | 80 |
| Asn | Thr | Arg | Glu | Thr | Ala | Cys | Tyr | Lys | Ala | Thr | Gly | Cys | Thr | Asn | Ala |
| | | | | 85 | | | | | 90 | | | | | 95 | |
| Ala | Leu | Ile | Cys | Leu | Leu | Lys | Gly | Pro | Thr | Leu | Glu | Glu | Asn | Gln | Lys |
| | | | 100 | | | | | 105 | | | | | 110 | | |
| Pro | Ile | Thr | Asp | Glu | Thr | Trp | Lys | Lys | Val | Leu | Asp | Val | Tyr | Gly | Glu |
| | | 115 | | | | | 120 | | | | | 125 | | | |
| Lys | Met | Asp | Phe | Lys | Glu | Arg | Glu | Glu | Gly | Glu | Ser | Cys | Leu | Thr | Glu |
| | 130 | | | | | 135 | | | | | 140 | | | | |
| Ile | Asn | Asp | Phe | Arg | Ala | Gln | Asp | Gly | Leu | Ala | Leu | Pro | Pro | Phe | Ala |
| 145 | | | | | 150 | | | | | 155 | | | | | 160 |
| Ala | Ala | Thr | Asp | Leu | His | Gly | Ala | Lys | Pro | Lys | Ala | Ser | Glu | Leu | Ile |
| | | | | 165 | | | | | 170 | | | | | 175 | |
| Gly | Lys | Gly | Leu | Thr | Cys | Glu | Ala | Leu | Lys | Ser | Gly | Asn | Ala | Pro | Ile |
| | | | 180 | | | | | 185 | | | | | 190 | | |
| Leu | Phe | Thr | Asp | Gln | Glu | Ile | Ser | Leu | Met | Tyr | Tyr | Met | Gly | Glu | Thr |
| | | 195 | | | | | 200 | | | | | 205 | | | |
| Ala | Thr | Cys | Ser | Leu | Ala | Val | Arg | Glu | Trp | Lys | Asn | Gly | Ile | Asp | Leu |
| | 210 | | | | | 215 | | | | | 220 | | | | |
| Phe | Ser | Asp | Phe | Thr | Ile | Pro | Pro | Lys | Tyr | Thr | Ser | Thr | Glu | Glu | Val |
| 225 | | | | | 230 | | | | | 235 | | | | | 240 |
| Tyr | Lys | Lys | Gly | Ala | Ala | Thr | Asn | Phe | Ile | Ser | Leu | Val | Ser | Glu | Gly |
| | | | | 245 | | | | | 250 | | | | | 255 | |
| Thr | Asp | Thr | Lys | Ile | Lys | Cys | Tyr | Thr | Val | Thr | Gly | Cys | Ser | Glu | Pro |
| | | | 260 | | | | | 265 | | | | | 270 | | |
| Gly | Leu | Leu | Cys | Leu | Leu | Gln | Pro | Pro | Val | Phe | Lys | Glu | Asn | Glu | Ala |
| | | 275 | | | | | 280 | | | | | 285 | | | |
| Pro | Ile | Ser | Glu | Glu | Thr | Trp | Lys | Lys | Val | Thr | Asp | Thr | Val | Thr | Ser |
| | 290 | | | | | 295 | | | | | 300 | | | | |
| Gly | Ala | Ala | Ser | Ala | Ser | Ala | Tyr | Gly | Ala | Leu | Leu | Ser | Ser | Val | Phe |
| 305 | | | | | 310 | | | | | 315 | | | | | 320 |
| Val | Ala | Val | Gly | Leu | Phe | Ala | Leu | Ser | Phe | | | | | | |
| | | | 325 | | | | | 330 | | | | | | | |

( 2 ) INFORMATION FOR SEQ ID NO:7:

( i ) SEQUENCE CHARACTERISTICS:
        ( A ) LENGTH: 800 base pairs (B) TYPE: nucleic acid
(C) STRANDEDNESS: double
(D) TOPOLOGY: linear (ii) MOLECULE TYPE: cDNA to mRNA (vii) IMMEDIATE SOURCE:
(B) CLONE: Eam20E (ix) FEATURE:
(A) NAME/KEY: CDS
(B) LOCATION: 2..508

(xi) SEQUENCE DESCRIPTION: SEQ ID NO:7:

| T | TTT | TGT | TTT | GCT | TTT | TCT | TGT | TTT | TTA | CTC | GGT | GTT | GGG | GCT | GGA | 46 |
|---|---|---|---|---|---|---|---|---|---|---|---|---|---|---|---|---|
|  | Phe | Cys | Phe | Ala | Phe | Ser | Cys | Phe | Leu | Leu | Gly | Val | Gly | Ala | Gly |  |
|  | 1 |  |  |  | 5 |  |  |  |  | 10 |  |  |  |  | 15 |  |

| TGG | TCT | TCA | AGC | TTC | TGG | GTT | GTT | GTT | GCA | TGC | ATG | TGG | CTG | ATA | CTT | 94 |
|---|---|---|---|---|---|---|---|---|---|---|---|---|---|---|---|---|
| Trp | Ser | Ser | Ser | Phe | Trp | Val | Val | Val | Ala | Cys | Met | Trp | Leu | Ile | Leu |  |
|  |  |  | 20 |  |  |  |  |  | 25 |  |  |  |  | 30 |  |  |

| TTC | TTC | GGA | GGG | TCT | CTT | CTT | CCT | GCT | GCT | ACT | GGG | GTT | GTT | ATT | GCT | 142 |
|---|---|---|---|---|---|---|---|---|---|---|---|---|---|---|---|---|
| Phe | Phe | Gly | Gly | Ser | Leu | Leu | Pro | Ala | Ala | Thr | Gly | Val | Val | Ile | Ala |  |
|  |  | 35 |  |  |  |  |  | 40 |  |  |  |  | 45 |  |  |  |

| TCT | GTT | CCT | GTT | GAA | GTT | AGA | GCA | TTC | GGC | AGC | GGT | TTT | TGT | TTA | ATG | 190 |
|---|---|---|---|---|---|---|---|---|---|---|---|---|---|---|---|---|
| Ser | Val | Pro | Val | Glu | Val | Arg | Ala | Phe | Gly | Ser | Gly | Phe | Cys | Leu | Met |  |
|  |  | 50 |  |  |  |  | 55 |  |  |  |  | 60 |  |  |  |  |

| GTT | TAT | AAT | GTC | GCT | GGC | TAT | GTC | CTC | GGT | CCC | TTC | TTA | CCT | GGC | ATA | 238 |
|---|---|---|---|---|---|---|---|---|---|---|---|---|---|---|---|---|
| Val | Tyr | Asn | Val | Ala | Gly | Tyr | Val | Leu | Gly | Pro | Phe | Leu | Pro | Gly | Ile |  |
|  | 65 |  |  |  |  | 70 |  |  |  |  | 75 |  |  |  |  |  |

| CTC | ATA | GAA | GCA | GCA | AAC | CTT | ACC | TGG | GGA | ATG | AGA | GTG | ATT | TAC | CTT | 286 |
|---|---|---|---|---|---|---|---|---|---|---|---|---|---|---|---|---|
| Leu | Ile | Glu | Ala | Ala | Asn | Leu | Thr | Trp | Gly | Met | Arg | Val | Ile | Tyr | Leu |  |
| 80 |  |  |  |  | 85 |  |  |  |  | 90 |  |  |  |  | 95 |  |

| TGG | TCT | ATT | AAT | GGC | GTT | CTC | GGG | TTT | GCA | TTA | GCG | TGC | TGC | TTC | CTC | 334 |
|---|---|---|---|---|---|---|---|---|---|---|---|---|---|---|---|---|
| Trp | Ser | Ile | Asn | Gly | Val | Leu | Gly | Phe | Ala | Leu | Ala | Cys | Cys | Phe | Leu |  |
|  |  |  |  | 100 |  |  |  |  | 105 |  |  |  |  | 110 |  |  |

| TGG | CGC | TTC | AAA | ATA | CAC | CCT | GCC | TTC | ATC | TCC | GAC | GAT | GAT | GAA | GAA | 382 |
|---|---|---|---|---|---|---|---|---|---|---|---|---|---|---|---|---|
| Trp | Arg | Phe | Lys | Ile | His | Pro | Ala | Phe | Ile | Ser | Asp | Asp | Asp | Glu | Glu |  |
|  |  |  | 115 |  |  |  |  | 120 |  |  |  |  | 125 |  |  |  |

| CCA | TGG | CAG | CAG | CAG | CAG | CAG | CAG | CAG | CAA | CAG | CAG | CAG | CAG | CAG | TTG | 430 |
|---|---|---|---|---|---|---|---|---|---|---|---|---|---|---|---|---|
| Pro | Trp | Gln | Gln | Gln | Gln | Gln | Gln | Gln | Gln | Gln | Gln | Gln | Gln | Gln | Leu |  |
|  |  | 130 |  |  |  |  | 135 |  |  |  |  | 140 |  |  |  |  |

| CAG | CTG | CAG | CAG | CTG | CAG | TTG | GAG | ACG | AAA | AGC | GAA | CTC | AGG | GAT | AGT | 478 |
|---|---|---|---|---|---|---|---|---|---|---|---|---|---|---|---|---|
| Gln | Leu | Gln | Gln | Leu | Gln | Leu | Glu | Thr | Lys | Ser | Glu | Leu | Arg | Asp | Ser |  |
|  | 145 |  |  |  |  | 150 |  |  |  |  | 155 |  |  |  |  |  |

| GAT | TCT | TGT | GTC | ACA | GCA | GCG | GCT | AAT | TGATGCGGTT | GCAACAAGCA | 525 |
|---|---|---|---|---|---|---|---|---|---|---|---|
| Asp | Ser | Cys | Val | Thr | Ala | Ala | Ala | Asn |  |  |  |
| 160 |  |  |  | 165 |  |  |  |  |  |  |  |

| GCAAGCCTTC | AATGGTAGTT | GCTCACTGAT | GTATTTCCTT | CTAGTTGAGT | TGTGTGCATG | 585 |
|---|---|---|---|---|---|---|
| CCAGCATGCA | TGCACGAACA | ACAGACTAGC | AGTGGCTCAT | CTGCTGCATG | CAGCTGCATG | 645 |
| CAACTGCATG | CAACTGAAAA | GCCCTGCGGA | GTTAAGCTGT | TTGTCTTTGC | TTCTTGTCTT | 705 |
| GTGCATCGGT | TGGCTGGCAT | GCGCTGCTGC | ATGCCCAGCG | AACCTTCTT | CGAAATATTC | 765 |
| TGCGGACACT | ATAAACTGAT | TTCTCTCCTT | CTTTG |  |  | 800 |

(2) INFORMATION FOR SEQ ID NO:8:

(i) SEQUENCE CHARACTERISTICS:
(A) LENGTH: 168 amino acids
(B) TYPE: amino acid
(D) TOPOLOGY: linear (ii) MOLECULE TYPE: protein (xi) SEQUENCE DESCRIPTION: SEQ ID NO:8:

| Phe | Cys | Phe | Ala | Phe | Ser | Cys | Phe | Leu | Leu | Gly | Val | Gly | Ala | Gly | Trp |
|---|---|---|---|---|---|---|---|---|---|---|---|---|---|---|---|
| 1 | | | | 5 | | | | | 10 | | | | | 15 | |

Ser Ser Ser Phe Trp Val Val Val Ala Cys Met Trp Leu Ile Leu Phe
            20                  25                  30

Phe Gly Gly Ser Leu Leu Pro Ala Ala Thr Gly Val Val Ile Ala Ser
        35                  40                      45

Val Pro Val Glu Val Arg Ala Phe Gly Ser Gly Phe Cys Leu Met Val
    50                  55                  60

Tyr Asn Val Ala Gly Tyr Val Leu Gly Pro Phe Leu Pro Gly Ile Leu
65                  70                  75                  80

Ile Glu Ala Ala Asn Leu Thr Trp Gly Met Arg Val Ile Tyr Leu Trp
            85                  90                  95

Ser Ile Asn Gly Val Leu Gly Phe Ala Leu Ala Cys Cys Phe Leu Trp
            100                 105                 110

Arg Phe Lys Ile His Pro Ala Phe Ile Ser Asp Asp Glu Glu Pro
        115                 120                 125

Trp Gln Gln Gln Gln Gln Gln Gln Gln Gln Gln Gln Gln Leu Gln
    130                 135                 140

Leu Gln Gln Leu Gln Leu Glu Thr Lys Ser Glu Leu Arg Asp Ser Asp
145                 150                 155                 160

Ser Cys Val Thr Ala Ala Ala Asn
                165

(2) INFORMATION FOR SEQ ID NO:9:

(i) SEQUENCE CHARACTERISTICS:
        (A) LENGTH: 2375 base pairs
        (B) TYPE: nucleic acid
        (C) STRANDEDNESS: single
        (D) TOPOLOGY: linear (ii) MOLECULE TYPE: cDNA to mRNA (vii) IMMEDIATE SOURCE:
        (B) CLONE: Eam100E (ix) FEATURE:
        (A) NAME/KEY: CDS
        (B) LOCATION: 3..1859

(xi) SEQUENCE DESCRIPTION: SEQ ID NO:9:

```
TC GGG GTT GCT AAG AGG GGA GAC GTC ACA GCT TGC AGG TAC TCC GAC      47
   Gly Val Ala Lys Arg Gly Asp Val Thr Ala Cys Arg Tyr Ser Asp
   1               5                  10                  15

TCC AGC TGT TAC TTG AGG AAT ATC GAG TAC ACT GGA GCA GCC TAC AAA     95
Ser Ser Cys Tyr Leu Arg Asn Ile Glu Tyr Thr Gly Ala Ala Tyr Lys
                20                  25                  30

GAC GTC AAG AAG AGC TAC TTA CAA GAG TGC CCG CAT TTG TGC GCC CTA    143
Asp Val Lys Lys Ser Tyr Leu Gln Glu Cys Pro His Leu Cys Ala Leu
            35                  40                  45

GAA GCA CGC TGT CAA CGC TGG ACA TAC AAC AAG ACC AAG AAA TCC TGC    191
Glu Ala Arg Cys Gln Arg Trp Thr Tyr Asn Lys Thr Lys Lys Ser Cys
        50                  55                  60

AGG CTC TTC GAT TTG GAA TCC TCT AAG GCC GGC ACC TAC ACC TCA CAA    239
Arg Leu Phe Asp Leu Glu Ser Ser Lys Ala Gly Thr Tyr Thr Ser Gln
65                  70                  75

CCC TCG TGG AGT GGC CCT AAG AAC GGC TGC GCT TCT GAA CCC CTG TAC    287
Pro Ser Trp Ser Gly Pro Lys Asn Gly Cys Ala Ser Glu Pro Leu Tyr
80                  85                  90                  95

AAT GCA TTT CAG AAT GTG CCT TCA TGC AGC ATG AGA GGC GTG CGC TAT    335
```

-continued

| | | | | | | | | | | | | | | |
|---|---|---|---|---|---|---|---|---|---|---|---|---|---|---|
|Asn|Ala|Phe|Gln|Asn|Val|Pro|Ser|Cys|Ser|Met|Arg|Gly|Val|Arg|Tyr|
| | | |100| | | |105| | | | |110| | |

```
GAC GGG GTG CCT TTT GCA GTT GAG AAA ACC GAG ACC GCA AAC GCA TGC        383
Asp Gly Val Pro Phe Ala Val Glu Lys Thr Glu Thr Ala Asn Ala Cys
            115             120             125

CAA GCT AAA TGC CAG ACG ACC ACA GGA TGT GAA GCC TTC TCT TAC GAT        431
Gln Ala Lys Cys Gln Thr Thr Thr Gly Cys Glu Ala Phe Ser Tyr Asp
        130             135             140

ATG AAA GGA GGA GTA TGC TAC ATG CAT ATT GCA TTT GCA GTG ATG TCG        479
Met Lys Gly Gly Val Cys Tyr Met His Ile Ala Phe Ala Val Met Ser
    145             150             155

AAG CGC CCC AAC TAC AAC TTC GTC TCA GGC CCG CGT CAA TGC GCA GGC        527
Lys Arg Pro Asn Tyr Asn Phe Val Ser Gly Pro Arg Gln Cys Ala Gly
160             165             170             175

TGC ATG AAG AAG GGT GTA GAG TAC AAC GGC GAA ATC ATC AGG GAG CTC        575
Cys Met Lys Lys Gly Val Glu Tyr Asn Gly Glu Ile Ile Arg Glu Leu
            180             185             190

ACC ACG GCA GTA GAG ACC GAA GAA GAG TGC CAG CTG CAC TGC CAA GCT        623
Thr Thr Ala Val Glu Thr Glu Glu Glu Cys Gln Leu His Cys Gln Ala
        195             200             205

ATA TCG ACC TGC GCT GTA TTC TCG TAC CGT GGA AGC TTC TGC AGA CTC        671
Ile Ser Thr Cys Ala Val Phe Ser Tyr Arg Gly Ser Phe Cys Arg Leu
    210             215             220

ATT GGA AGA GAT GCT ACA ACC GAG CAA AGC CCC CTA GCA ACA AGC GGC        719
Ile Gly Arg Asp Ala Thr Thr Glu Gln Ser Pro Leu Ala Thr Ser Gly
225             230             235

ACG AAG CAC TGT GCA GGA GAT TGC TAT CTG CAA GGT GTC CAT AGC CCA        767
Thr Lys His Cys Ala Gly Asp Cys Tyr Leu Gln Gly Val His Ser Pro
240             245             250             255

CGG CGT GAT TAC GGG TAC GTG AAG GAA TTG AGC GGC AAG ACA GCT GAA        815
Arg Arg Asp Tyr Gly Tyr Val Lys Glu Leu Ser Gly Lys Thr Ala Glu
            260             265             270

CAG TGC CGC GAC ACG TGC AAA GCA GAT GAG AAG TGC ACG AGC TTC ACA        863
Gln Cys Arg Asp Thr Cys Lys Ala Asp Glu Lys Cys Thr Ser Phe Thr
        275             280             285

CAC TGG AAT GAC AAA CGG TGC TAC TTG AAA GAT GAC GAG TCC TTC AGA        911
His Trp Asn Asp Lys Arg Cys Tyr Leu Lys Asp Asp Glu Ser Phe Arg
    290             295             300

TAT CTT TCA CCT ATC GAG GGG GCC GTC ACA GGC TTC CCA ACC TGC TCT        959
Tyr Leu Ser Pro Ile Glu Gly Ala Val Thr Gly Phe Pro Thr Cys Ser
305             310             315

ATC TGC ATG AGG GAA GGA GTA AGG ATC CTA GCA AAC GAT TCG AAT CTC       1007
Ile Cys Met Arg Glu Gly Val Arg Ile Leu Ala Asn Asp Ser Asn Leu
320             325             330             335

CTG TGG AAC TTG GAA GCC GGC AAT GCA GAA GAA TGT AAG ATT CGC TGC       1055
Leu Trp Asn Leu Glu Ala Gly Asn Ala Glu Glu Cys Lys Ile Arg Cys
            340             345             350

GGA CTC ATG AGC TCG TGC ACT CGC TTT GCT TTC AAT ATA GTG ACA AAG       1103
Gly Leu Met Ser Ser Cys Thr Arg Phe Ala Phe Asn Ile Val Thr Lys
        355             360             365

CAA TGC AGT CTT CTC TCA GGC GAA GGC GAG TTG GTG GAA GCA CGT GAC       1151
Gln Cys Ser Leu Leu Ser Gly Glu Gly Glu Leu Val Glu Ala Arg Asp
    370             375             380

TAC GTC TCC GGG CCC GCT AAA TGC TTA ACG GAC ATC TCT TGC TTC CAG       1199
Tyr Val Ser Gly Pro Ala Lys Cys Leu Thr Asp Ile Ser Cys Phe Gln
385             390             395

AGA GAT GTC GCT TTC ACT GGC GGC GAG ACA GTT GCT ACA GAT GTG ACA       1247
Arg Asp Val Ala Phe Thr Gly Gly Glu Thr Val Ala Thr Asp Val Thr
400             405             410             415

GAG AAC GCA GGG CTC TGC ATG CGG TGG TGT GCA AAG GAA GCA CAA TGC       1295
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| Glu | Asn | Ala | Gly | Leu | Cys | Met | Arg | Trp | Cys | Ala | Lys | Glu | Ala | Gln | Cys |      |
|     |     |     |     | 420 |     |     |     | 425 |     |     |     |     |     | 430 |     |      |
| ACG | CAC | TTC | ACC | TTT | ACT | TTT | GCT | GAA | GAT | CGT | CTC | TCC | GGC | CAA | TGC | 1343 |
| Thr | His | Phe | Thr | Phe | Thr | Phe | Ala | Glu | Asp | Arg | Leu | Ser | Gly | Gln | Cys |      |
|     |     |     | 435 |     |     |     |     | 440 |     |     |     |     | 445 |     |     |      |
| ACT | CTT | CTT | AAG | GGG | GAT | CTG | AAT | GTA | ACG | AAA | ACT | AAG | GGT | GCT | GTC | 1391 |
| Thr | Leu | Leu | Lys | Gly | Asp | Leu | Asn | Val | Thr | Lys | Thr | Lys | Gly | Ala | Val |      |
|     |     | 450 |     |     |     |     | 455 |     |     |     |     | 460 |     |     |     |      |
| TCA | GGC | CCA | AAG | CGG | TGT | TTC | GAA | CTG | CTC | TCT | CTC | TGC | GAG | GAA | CCA | 1439 |
| Ser | Gly | Pro | Lys | Arg | Cys | Phe | Glu | Leu | Leu | Ser | Leu | Cys | Glu | Glu | Pro |      |
|     | 465 |     |     |     |     | 470 |     |     |     |     | 475 |     |     |     |     |      |
| GAT | GTA | GAG | TAT | GTC | GGA | GGT | GAG | ATC | TCC | AAC | GTG | GAT | GCA | GAA | GAT | 1487 |
| Asp | Val | Glu | Tyr | Val | Gly | Gly | Glu | Ile | Ser | Asn | Val | Asp | Ala | Glu | Asp |      |
| 480 |     |     |     |     | 485 |     |     |     |     | 490 |     |     |     |     | 495 |      |
| ACA | ACA | CAG | TGC | AGA | GAG | CTC | TGC | TAC | AAA | CAC | CCG | ATG | TGC | CGG | CTC | 1535 |
| Thr | Thr | Gln | Cys | Arg | Glu | Leu | Cys | Tyr | Lys | His | Pro | Met | Cys | Arg | Leu |      |
|     |     |     |     | 500 |     |     |     |     | 505 |     |     |     |     | 510 |     |      |
| TAT | ACA | TTC | ACC | CCA | GCG | GAG | AAG | AAG | TGC | TCA | CTG | AAG | AAG | ATT | GAA | 1583 |
| Tyr | Thr | Phe | Thr | Pro | Ala | Glu | Lys | Lys | Cys | Ser | Leu | Lys | Lys | Ile | Glu |      |
|     |     |     | 515 |     |     |     |     | 520 |     |     |     |     | 525 |     |     |      |
| GCT | GTT | GCA | GGA | CGT | ACA | ACG | AAA | AAA | CAA | GGC | AAA | GTA | TCT | GGA | TCT | 1631 |
| Ala | Val | Ala | Gly | Arg | Thr | Thr | Lys | Lys | Gln | Gly | Lys | Val | Ser | Gly | Ser |      |
|     |     | 530 |     |     |     |     | 535 |     |     |     |     | 540 |     |     |     |      |
| AAG | GTA | GGG | TGC | GCT | CGT | AGT | GCT | AGA | GGT | GGC | TAT | GCT | TAT | AAA | GGA | 1679 |
| Lys | Val | Gly | Cys | Ala | Arg | Ser | Ala | Arg | Gly | Gly | Tyr | Ala | Tyr | Lys | Gly |      |
|     | 545 |     |     |     |     | 550 |     |     |     |     | 555 |     |     |     |     |      |
| ACC | TCC | TTC | AAG | ACT | ATT | CCG | GGC | TTA | CCT | CAT | GAG | ACA | GCC | TGC | CGG | 1727 |
| Thr | Ser | Phe | Lys | Thr | Ile | Pro | Gly | Leu | Pro | His | Glu | Thr | Ala | Cys | Arg |      |
| 560 |     |     |     |     | 565 |     |     |     |     | 570 |     |     |     |     | 575 |      |
| CTG | CAA | TGC | GAA | TAC | GAG | AGC | AAC | TGC | ATT | GCT | TTC | ACC | TTC | GAC | ACC | 1775 |
| Leu | Gln | Cys | Glu | Tyr | Glu | Ser | Asn | Cys | Ile | Ala | Phe | Thr | Phe | Asp | Thr |      |
|     |     |     |     | 580 |     |     |     |     | 585 |     |     |     |     | 590 |     |      |
| GAG | AAG | AAG | GTG | TGC | TCT | CTT | AAG | GCC | CGC | GTG | GAC | TTA | GTA | GAA | CCC | 1823 |
| Glu | Lys | Lys | Val | Cys | Ser | Leu | Lys | Ala | Arg | Val | Asp | Leu | Val | Glu | Pro |      |
|     |     |     | 595 |     |     |     |     | 600 |     |     |     |     | 605 |     |     |      |
| AGA | GAT | ACA | GGT | GTT | ATT | GGG | CCT | AAA | CGC | GAA | TAAACAGCTG | CTAATAATGT |  |  |  | 1876 |
| Arg | Asp | Thr | Gly | Val | Ile | Gly | Pro | Lys | Arg | Glu |     |     |     |     |     |      |
|     |     | 610 |     |     |     |     | 615 |     |     |     |     |     |     |     |     |      |

```
AATTGAAGCT GTTGCTTCTT CTGCTGGAGC TTGTGCTTGT CGCTCGCTGC ACGAGAACAC   1936
TGGCAGGCAT CGATTCGCAG CTGTATCTCG GTCGGCTTCA TGGTTACTTC CATGTTAGCG   1996
ACTGCACTGC ATTGCTTTCT TCTTTCTCT  TCTCTATTCC CCTCACTTCT TAGCCTGCAT   2056
CCCAAAGGGT TCAGGCATTC AAGAGAAGAG GGTGCTCTCT TCTTTCTCAC GGTGCAGATA   2116
CACGAGACGT AAATAAACAC AATTAACAAA ACACACCCAC AGCGAGGACA GAACATCATC   2176
AGCATTTATA TCACTGCGTT GCATGCATTT AATAACGGCA AGAACGACAG GGGAGCGAGC   2236
GACACAGCAG TCTAGACGTC GCTCTGTGCT CCCTTGCAAG ATGTCTTTTC GCATACATCA   2296
AACAGAAGAA AAGAAAGACG TGCAGTTTGA ACTGACGTTT GTTCATGCAT GCATGCATGC   2356
AAAAAAAAAA AGGCACGAG                                                2375
```

( 2 ) INFORMATION FOR SEQ ID NO:10:

( i ) SEQUENCE CHARACTERISTICS:
        ( A ) LENGTH: 618 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

| | | | | | | | | | | | | | | | |
|---|---|---|---|---|---|---|---|---|---|---|---|---|---|---|---|
| Gly | Val | Ala | Lys | Arg | Gly | Asp | Val | Thr | Ala | Cys | Arg | Tyr | Ser | Asp | Ser |
| 1 | | | | 5 | | | | | 10 | | | | | 15 | |
| Ser | Cys | Tyr | Leu | Arg | Asn | Ile | Glu | Tyr | Thr | Gly | Ala | Ala | Tyr | Lys | Asp |
| | | | 20 | | | | | 25 | | | | | 30 | | |
| Val | Lys | Lys | Ser | Tyr | Leu | Gln | Glu | Cys | Pro | His | Leu | Cys | Ala | Leu | Glu |
| | | 35 | | | | | 40 | | | | | 45 | | | |
| Ala | Arg | Cys | Gln | Arg | Trp | Thr | Tyr | Asn | Lys | Thr | Lys | Lys | Ser | Cys | Arg |
| | 50 | | | | | 55 | | | | | 60 | | | | |
| Leu | Phe | Asp | Leu | Glu | Ser | Ser | Lys | Ala | Gly | Thr | Tyr | Thr | Ser | Gln | Pro |
| 65 | | | | | 70 | | | | | 75 | | | | | 80 |
| Ser | Trp | Ser | Gly | Pro | Lys | Asn | Gly | Cys | Ala | Ser | Glu | Pro | Leu | Tyr | Asn |
| | | | | 85 | | | | | 90 | | | | | 95 | |
| Ala | Phe | Gln | Asn | Val | Pro | Ser | Cys | Ser | Met | Arg | Gly | Val | Arg | Tyr | Asp |
| | | | 100 | | | | | 105 | | | | | 110 | | |
| Gly | Val | Pro | Phe | Ala | Val | Glu | Lys | Thr | Glu | Thr | Ala | Asn | Ala | Cys | Gln |
| | | | 115 | | | | | 120 | | | | | 125 | | |
| Ala | Lys | Cys | Gln | Thr | Thr | Thr | Gly | Cys | Glu | Ala | Phe | Ser | Tyr | Asp | Met |
| | 130 | | | | | 135 | | | | | 140 | | | | |
| Lys | Gly | Gly | Val | Cys | Tyr | Met | His | Ile | Ala | Phe | Ala | Val | Met | Ser | Lys |
| 145 | | | | | 150 | | | | | 155 | | | | | 160 |
| Arg | Pro | Asn | Tyr | Asn | Phe | Val | Ser | Gly | Pro | Arg | Gln | Cys | Ala | Gly | Cys |
| | | | | 165 | | | | | 170 | | | | | 175 | |
| Met | Lys | Lys | Gly | Val | Glu | Tyr | Asn | Gly | Glu | Ile | Ile | Arg | Glu | Leu | Thr |
| | | | 180 | | | | | 185 | | | | | 190 | | |
| Thr | Ala | Val | Glu | Thr | Glu | Glu | Cys | Gln | Leu | His | Cys | Gln | Ala | Ile |
| | | 195 | | | | | 200 | | | | | 205 | | | |
| Ser | Thr | Cys | Ala | Val | Phe | Ser | Tyr | Arg | Gly | Ser | Phe | Cys | Arg | Leu | Ile |
| | 210 | | | | | 215 | | | | | 220 | | | | |
| Gly | Arg | Asp | Ala | Thr | Thr | Glu | Gln | Ser | Pro | Leu | Ala | Thr | Ser | Gly | Thr |
| 225 | | | | | 230 | | | | | 235 | | | | | 240 |
| Lys | His | Cys | Ala | Gly | Asp | Cys | Tyr | Leu | Gln | Gly | Val | His | Ser | Pro | Arg |
| | | | | 245 | | | | | 250 | | | | | 255 | |
| Arg | Asp | Tyr | Gly | Tyr | Val | Lys | Glu | Leu | Ser | Gly | Lys | Thr | Ala | Glu | Gln |
| | | | 260 | | | | | 265 | | | | | 270 | | |
| Cys | Arg | Asp | Thr | Cys | Lys | Ala | Asp | Glu | Lys | Cys | Thr | Ser | Phe | Thr | His |
| | | 275 | | | | | 280 | | | | | 285 | | | |
| Trp | Asn | Asp | Lys | Arg | Cys | Tyr | Leu | Lys | Asp | Asp | Glu | Ser | Phe | Arg | Tyr |
| | 290 | | | | | 295 | | | | | 300 | | | | |
| Leu | Ser | Pro | Ile | Glu | Gly | Ala | Val | Thr | Gly | Phe | Pro | Thr | Cys | Ser | Ile |
| 305 | | | | | 310 | | | | | 315 | | | | | 320 |
| Cys | Met | Arg | Glu | Gly | Val | Arg | Ile | Leu | Ala | Asn | Asp | Ser | Asn | Leu | Leu |
| | | | | 325 | | | | | 330 | | | | | 335 | |
| Trp | Asn | Leu | Glu | Ala | Gly | Asn | Ala | Glu | Glu | Cys | Lys | Ile | Arg | Cys | Gly |
| | | | 340 | | | | | 345 | | | | | 350 | | |
| Leu | Met | Ser | Ser | Cys | Thr | Arg | Phe | Ala | Phe | Asn | Ile | Val | Thr | Lys | Gln |
| | | 355 | | | | | 360 | | | | | 365 | | | |
| Cys | Ser | Leu | Leu | Ser | Gly | Glu | Gly | Glu | Leu | Val | Glu | Ala | Arg | Asp | Tyr |
| | 370 | | | | | 375 | | | | | 380 | | | | |
| Val | Ser | Gly | Pro | Ala | Lys | Cys | Leu | Thr | Asp | Ile | Ser | Cys | Phe | Gln | Arg |
| 385 | | | | | 390 | | | | | 395 | | | | | 400 |
| Asp | Val | Ala | Phe | Thr | Gly | Gly | Glu | Thr | Val | Ala | Thr | Asp | Val | Thr | Glu |
| | | | | 405 | | | | | 410 | | | | | 415 | |
| Asn | Ala | Gly | Leu | Cys | Met | Arg | Trp | Cys | Ala | Lys | Glu | Ala | Gln | Cys | Thr |

|     |     | 420 |     |     |     |     | 425 |     |     |     |     | 430 |     |     |     |
| --- | --- | --- | --- | --- | --- | --- | --- | --- | --- | --- | --- | --- | --- | --- | --- |
| His | Phe | Thr 435 | Phe | Thr | Phe | Ala | Glu 440 | Asp | Arg | Leu | Ser | Gly 445 | Gln | Cys | Thr |
| Leu | Leu 450 | Lys | Gly | Asp | Leu | Asn 455 | Val | Thr | Lys | Thr | Lys 460 | Gly | Ala | Val | Ser |
| Gly 465 | Pro | Lys | Arg | Cys | Phe 470 | Glu | Leu | Leu | Ser | Leu 475 | Cys | Glu | Glu | Pro | Asp 480 |
| Val | Glu | Tyr | Val | Gly 485 | Gly | Glu | Ile | Ser | Asn 490 | Val | Asp | Ala | Glu | Asp 495 | Thr |
| Thr | Gln | Cys | Arg 500 | Glu | Leu | Cys | Tyr | Lys 505 | His | Pro | Met | Cys | Arg 510 | Leu | Tyr |
| Thr | Phe | Thr 515 | Pro | Ala | Glu | Lys | Lys 520 | Cys | Ser | Leu | Lys | Lys 525 | Ile | Glu | Ala |
| Val | Ala 530 | Gly | Arg | Thr | Thr | Lys 535 | Lys | Gln | Gly | Lys | Val 540 | Ser | Gly | Ser | Lys |
| Val 545 | Gly | Cys | Ala | Arg | Ser 550 | Ala | Arg | Gly | Gly | Tyr 555 | Ala | Tyr | Lys | Gly | Thr 560 |
| Ser | Phe | Lys | Thr | Ile 565 | Pro | Gly | Leu | Pro | His 570 | Glu | Thr | Ala | Cys | Arg 575 | Leu |
| Gln | Cys | Glu | Tyr 580 | Glu | Ser | Asn | Cys | Ile 585 | Ala | Phe | Thr | Phe | Asp 590 | Thr | Glu |
| Lys | Lys | Val 595 | Cys | Ser | Leu | Lys | Ala 600 | Arg | Val | Asp | Leu | Val 605 | Glu | Pro | Arg |
| Asp | Thr 610 | Gly | Val | Ile | Gly | Pro 615 | Lys | Arg | Glu |     |     |     |     |     |     |

DNA ENCODING AN EIMERIA 100KD ANTIGEN

This is a division of application U.S. Ser. No. 08/310,357, filed Sep. 21, 1994, which is a file wrapper continuation of U.S. Ser. No. 08/102,865, filed Aug. 6, 1993, now abandoned, which is a file wrapper continuation of U.S. Ser. No. 07/904,075, filed Jun. 18, 1992, now abandoned.

The present invention is concerned with a protein having one or more immunogenic determinants of an Eimeria antigen, a nucleic acid sequence encoding this protein, a recombinant vector molecule or recombinant vector virus comprising such a nucleic acid sequence, a host cell transformed with such a recombinant vector molecule or infected with the recombinant vector virus, antibodies immunoreactive with said protein, as well as a vaccine for the protection of avians against coccidiosis.

BACKGROUND OF THE INVENTION

Coccidiosis is a disease which is caused by intracellular parasites, protozoa, of the subphylum Apicomplexa and the genus Eimeria. These parasites multiply in cells which form part of the gastrointestinal tract and digestive organs.

Due to the increase in intensive production, the damage which is caused by these parasites in the poultry industry has risen alarmingly in recent decades. For example, the losses which poultry farmers in the Netherlands suffer every year run into millions of guilders; the loss in 1986 was about 13 million guilders; in the same year a loss of U.S.$ 300 million was suffered in the U.S., despite the use of coccidio-stats.

The pathogens of coccidiosis in chickens can be subdivided into nine different species, i.e. *Eimeria acervulina, E. maxima, E. tenella, E. necatrix, E. brunetti, E. mitis, E. praecox, E. mivati* and *E. hagani*. However, some people doubt the existence of the last two species. All of these species have only the chicken as host and display a high degree of tissue specificity. The life cycles of the said species are, however, similar.

The species do differ in their pathogenic effect on chickens, the type of chicken also playing a role; thus, a broiler chicken will be subjected to a great deal of damage by a parasite such as *E. acervulina* or *E. maxima* because these parasitise large portions of the small intestine, where food digestion plays a major role.

During the life cycle, the Eimeria parasites pass through a number of stages. The infectious stage (the sporulating oocyst) is taken in orally and passes into the stomach of the chicken, where the wall of the cyst bursts open as a result of the grinding action. The four sporocysts, which this oocyst contains, are released and pass into the duodenum, where they are exposed to bile and digestive enzymes. As a result, an opening is made in the sporocyst wall and the sporozoites present in the sporocyst are released. These sporozoites are mobile and search for suitable host cells, epithelium cells, in order to penetrate and to reproduce. Depending on the species, this first reproduction phase lasts 20 to 48 hours and several tens to hundreds of merozoites are formed, which each again penetrate a new host cell and reproduce. After two to sometimes five of these asexual reproduction cycles, depending on the species the intracellular merozoites grow into sexual forms, the male and female gametocytes. After fertilization of the female by a male gamete, a zygote is formed which creates a cyst wall about itself. This oocyst leaves the host cell and is driven out with the faeces. If the temperature and humidity outside the chicken are relatively high and, at the same time, there is sufficient oxygen in the air, the oocyst can sporulate to the infectious stage.

Thus, no intermediate host is needed for transfer of the parasite from chicken to chicken. It is therefore conceivable that with a high degree of occupation of the available surface area the infection pressure in a chicken farm rapidly increases.

The parasite can be combatted in various ways.

In addition to using good management, coccidiosis can be controlled by using coccidiostatic agents which frequently are mixed in the feed or drinking water. However, these agents have suffered a drop in effectiveness in recent years, partly because of the high genetic capacity of the parasite to develop resistance against various combatting agents. In addition, a number of these agents leave residues in the meat which can give rise to problems on consumption.

Immunological prophylaxis would, therefore, constitute a much better combatting method. It is known that chickens which have lived through a sufficiently high infection are able to resist a subsequent contact with the same type of Eimeria. Resistance towards Eimeria can also be induced by infecting the birds several times with low doses of oocysts or with oocysts of weakened (non-pathogenic) strains. However, controlled administration to, specifically, large numbers of broiler chickens is a virtually insurmountable problem in this case.

BRIEF DESCRIPTION OF THE INVENTION

According to the present invention purified proteins having one or more immunogenic determinants of an Eimeria antigen, essentially free from the whole parasite or other protein with which they are ordinarily associated are provided which can be used for the preparation of a vaccine for the immunization of avians, in particular poultry against coccidiosis.

The invention is also concerned with a nucleic acid sequence encoding these proteins, a recombinant vector molecule or recombinant vector virus comprising such a nucleic acid sequence, a host cell transformed with such a recombinant vector molecule or infected with the recombinant vector virus, antibodies immunoreactive with said protein, as well as a vaccine for the protection of avians against coccidiosis.

DETAILED DESCRIPTION OF THE INVENTION

Figure 1A:
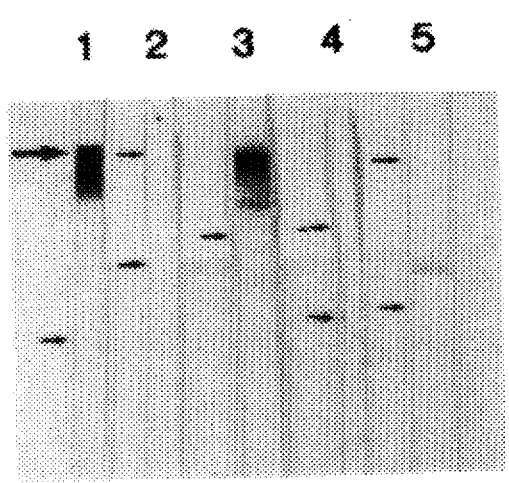
FIG. 1A & B is a panel of different Eimeria species and stages reacting with monoclonal antibodies E.ACER 11A-2A (Panel A) and E.ACER 12B-2B (Panel B).

"Nucleic acid sequence" as used herein refers to a polymeric form of nucleotides of any length, both to ribonucleic acid sequences and to deoxy ribonucleic acid sequences. In principle, this term refers to the primary structure of the molecule. Thus, this term includes double and single stranded DNA, as well as double and single stranded RNA, and modifications thereof.

In general, the term "protein" refers to a molecular chain of amino acids with a biological activity, does not refer to a specific length of the product and if required can be modified in vivo or in vitro, for example by glycosylation, amidation, carboxylation or phosphorylation; thus inter alia, peptides, oligopeptides and polypeptides are included.

The term "protein having one or more immunogenic determinants of an Eimeria antigen" refers to a protein having one or more epitopes capable of eliciting an immune response against Eimeria parasites in host animals.

The term "molecular weight" is used herein as an apparent size estimation under the circumstances described in the individual examples. The true molecular mass can only be determined after sequencing the full length protein. For individual proteins the apparent molecular weight estimated with SDS-PAGE can be erroneous due to hydrophobicity of the protein, or to the presence of oligosaccharides, lipids (acyl chains) or other interfering substitutes. Even the percentage of acrylamide gel used can influence the mobility in the gel relative to water-soluble marker proteins. An example is described in Frank, R. N. and Rodbard, D. (1975) Arch. Biochem. Biophys. 171, 1–13. Apart from these limitations most of the SDS-PAGE (Western blots) runs performed for this application were carried out non-reduced (so without the addition of beta-mercapthoethanol or dithiotreitol) for purpose of better recognition by Mabs.

In particular, the invention provides proteins having one or more immunogenic determinants of an Eimeria antigen wherein the Eimeria antigen has a molecular weight in SDS-PAGE of about 200, 100, 50 or 20 kD and the Eimeria antigen specifically binds with monoclonal antibody E.ACER 11A-2A or E.ACER 12B-2B, E.ACER 5F-2, E.ACER 10C-2A or E.ACER 10E-2, respectively. Samples of the hybridoma cell lines producing these monoclonal antibodies were deposited with the European Collection of Animal Cell Cultures (ECACC) at Porton Down, UK, under the accession No. 91061223 (E.ACER 12B-2B), 91061222 (E.ACER 11A-2A), 91061219 (E.ACER 5F-2), 91061220 (E.ACER 10C-2A) and 91061221 (E.ACER 10E-2).

The Eimeria antigens disclosed above can be characterized by their isolation procedure, i.e. the antigens are obtainable by:

1. extracting Eimeria acervulina parasites with a 2% Triton X114 solution, 2A. applying the hydrophobic fraction obtained after phase separation from step 1. to
  1. E.ACER 10C-2A sepharose CL-4B bound immuno-affinity chromatography, or to
  2. E.ACER 10E-2 sepharose CL-4B bound immuno-affinity chromatography, or 2B. applying the hydrophilic fraction obtained after phase separation from step 1. to E.ACER 11A-2A sepharose CL-4B bound immuno-affinity chromatography, or 2C. applying the hydrophilic fraction obtained after phase separation from step 1. to E.ACER 5F-2 sepharose CL-4B bound immuno-affinity chromatography, 3. 1. eluting the purified 50, 100 or 200 kD Eimeria protein with 0.1M glycine/HCl+0.1% NP40 pH 2.6, or 2. eluting the purified 20 kD Eimeria protein with 3M KSCN in 25 mM Tris/HCl+0.5M NaCl+0.1% NP40 pH 8.0.

Preferred proteins according to the invention comprise one or more immunogenic determinants of the Eimeria acervulina antigens Eam200, Eam100 or Eas100, Eam45 or Eam20 (Example 2).

Eam200 is an Eimeria protein of about 200 kD purified from Eimeria acervulina merozoites and is immuno-reactive with monoclonal antibody (Mab) E.ACER 11A-2A.

Eas100 is an Eimeria protein of about 100 kD purified from Eimeria acervulina sporozoites and is immuno-reactive with Mab E.ACER 5F-2, Eam100 is the merozoite equivalent.

Eam45 is an Eimeria protein of about 50 kD purified from Eimeria acervulina merozoites and is immuno-reactive with Mab E.ACER 10C-2A.

Eam20 is an Eimeria protein of about 20 kD purified from Eimeria acervulina merozoites and is immuno-reactive with Mab E.ACER 10E-2.

Monoclonal antibodies E.ACER 11A-2A and E.ACER 12B-2B are primarily directed against the Eam200 antigen. As is illustrated in FIG. 1 E.ACER 12B-2B recognised this protein in reduced as well as non-reduced form, panel B lanes 1 and 2. E-ACER 11A-2A recognised only the non-reduced form, panel A, lanes 1 and 2.

Both Mabs, however, recognised a set of polypeptides of MW 100 to 200 kD in E.acervulina sporozoites and a clear positive band of MW±130 kD in E.tenella sporozoites, lanes 3 and 5.

Using fluorescence the cross-reaction to sporozoites was limited to the anterior end of the sporozoite, where the organelles involved in invasion are localised.

E.tenella second generation merozoites did not appear to bind these Mabs probably due to the low abundance of the protein in that stage.

Figure 2A:
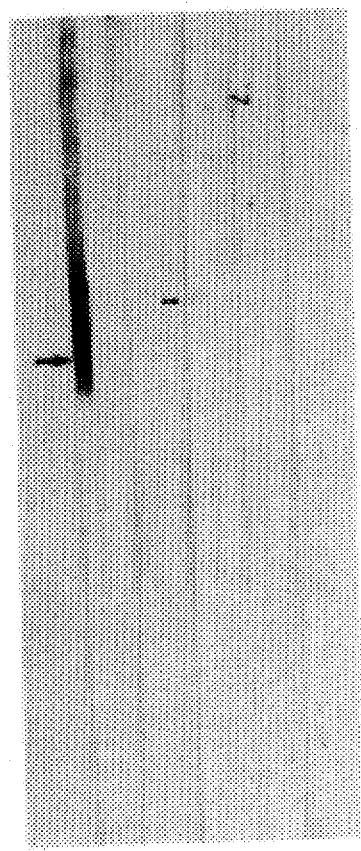
FIG. 2A & B is a panel of different Eimeria species and stages reacting with monoclonal antibodies E.ACER 10C-2A (Panel A) and E.ACER 10E-2 (Panel B).
Figure 2B:
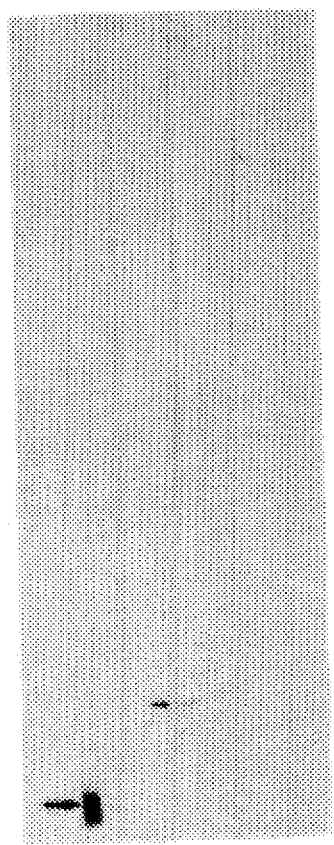

Monoclonal antibody E.ACER 10C-2A anti Eam45, only recognised a protein of similar molecular weight in sporozoites of E.acervulina and no reaction was found against E.tenella as illustrated in FIG. 2 panel A.

E.ACER 10E-2, anti Eam20, also recognised a faint band (MW±20 kD) in sporozoites of the homologous species only, although apart from E.acervulina and E.tenella no other species were tested, see FIG. 2 panel B.

Monoclonal E.ACER 5F-2 was raised against E.acervulina sporozoites but also recognised a protein of ±100 kD in merozoites of the homologous species. Reactivity against other species has not been tested.

More particularly, this invention provides examples of proteins having one or more immunogenic determinants of the purified Eimeria antigens identified above. These examples are proteins comprising the amino acid sequence shown in SEQ ID NO.: 2, 6, 8 or 10 and its functional variants.

Figure 9:
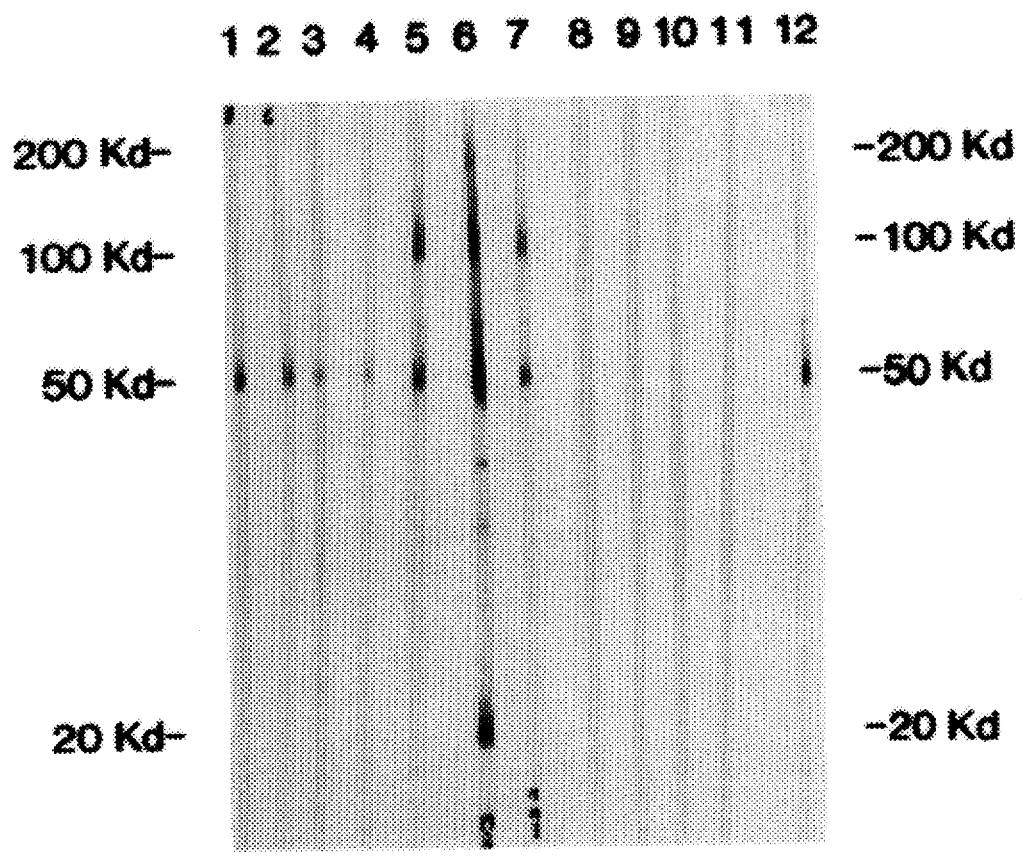
FIG. 9 depicts the reaction of clone Eam45 (M3)-selected antibodies on Western blot strips of *E. acervulina* proteins.

In addition, the present invention provides an Eimeria protein having the amino acid sequence shown in SEQ ID NO. 4 and its functional variant. This protein was identified by screening an Eimeria merozoite cDNA library with anti-Eam45 serum. This serum demonstrated a positive reaction with an about 100 kD protein (in addition to a positive reaction with the about 50 kD protein) when probing this serum back on a merozoite blot (FIG. 9).

The functional variants of the proteins specifically disclosed herein are proteins derived from the above-noted amino acid sequences, for example by deletions, insertions and/or substitutions of one or more amino acids, but retain one or more immunogenic determinants of the Eimeria antigens, i.e. said variants have one or more epitopes capable of eliciting an immune response in a host animal.

It will be understood that for the particular proteins embraced herein, natural variations can exist between individual Eimeria parasites or strains. These variations may be demonstrated by (an) amino acid difference(s) in the overall sequence or by deletions, substitutions, insertions, inversions or additions of (an) amino acid(s) in said sequence. Amino acid substitutions from which can be expected that they do not essentially alter biological and immunological activities, have been described. Amino acid replacements between related amino acids or replacements which have occurred frequently in evolution are, inter alia Ser/Ala, Ser/Gly, Asp/Gly, Asp/Asn, Ile/Val (see Dayhof, M. D., Atlas of protein sequence and structure, Nat. Biomed. Res. Found., Washington D.C., 1978, vol. 5, suppl. 3). Based on this information Lipman and Pearson developed a method for rapid and sensitive protein comparison (Science 227, 1435–1441, 1985) and determining the functional similarity between homologous proteins.

Furthermore, also immunogenic fragments of the proteins specifically disclosed herein or their functional variants are included in the present invention.

The term "fragment" as used herein means a DNA or amino acid sequence comprising a subsequence of the nucleic acid sequence or protein of the invention. Said fragment is or encodes a polypeptide having one or more immunogenic determinants of an Eimeria antigen. Methods for determining usable immunogenic polypeptide fragments are outlined below. Fragments can inter alia be produced by enzymatic cleavage of precursor molecules, using restriction endonucleases for the DNA and proteases for the polypeptides. Other methods include chemical synthesis of the fragments or the expression of polypeptide fragments by DNA fragments.

Suitable immunogenic polypeptide fragments of a protein according to the invention containing (an) epitope(s) can be found by means of the method described in Patent Application WO 86/06487, Geysen, H. M. et al. (Proc. Natl. Acad. Sci. 81, 3998–4002, 1984), Geysen, H. M. et al. (J. Immunol. Meth. 102, 259–274, 1987) based on the so-called pepscan method, wherein a series of partially overlapping peptides corresponding with partial sequences of the complete polypeptide under consideration, are synthesized and their reactivity with antibodies is investigated.

In addition, a number of regions of the polypeptide, with the stated amino acid sequence, can be designated epitopes on the basis of theoretical considerations and structural agreement with epitopes which are now known. The determination of these regions is based on a combination of the hydrophilicity criteria according to Hopp and Woods (Proc. Natl. Acad. Sci. 78, 3824–3828, 1981) and the secondary structure aspects according to Chou and Fasman (Advances in Enzymology 47, 45–148, 1987).

T-cell epitopes which may be necessary can likewise be derived on theoretical grounds, e.g. with the aid of Berzofsky's amphiphilicity criterion (Science 235, 1059–62, 1987).

The invention further provides isolated and purified nucleic acid sequences encoding the above-noted proteins of Eimeria.

As is well known in the art, the degeneracy of the genetic code permits substitution of bases in a codon resulting in an other codon but still coding for the same amino acid, e.g. the codon for the amino acid glutamic acid is both GAT and GAA. Consequently, it is clear that for the expression of a protein with the amino acid sequence shown in SEQ ID NO's: 2, 4, 6, 8 or 10 use can be made of a derivate nucleic acid sequence with such an alternative codon composition different from the nucleic acid sequence shown in SEQ ID NO's: 1, 3, 5, 7 or 9 respectively.

Therefore, the present invention particularly provides nucleic acid sequences encoding at least part of the proteins having the amino acid sequence shown in SEQ ID NO's.: 2, 4, 6, 8 or 10 and their functional variants.

The information provided in SEQ ID NO's: 1, 3, 5, 7 and 9 allows a person skilled in the art to isolate and identify the nucleic acid sequences encoding the various functional variant proteins mentioned above having corresponding immunological characteristics with the Eimeria proteins specifically disclosed herein. The generally applied Southern blotting technique or colony hybridization can be used for that purpose (Experiments in Molecular Biology, ed. R. J. Slater, Clifton, U.S.A., 1986; Singer-Sam, J. et al., Proc. Natl., Acad. Sci. 80, 802–806, 1983; Maniatis T. et al., Molecular Cloning, A laboratory Manual, second edition, Cold Spring Harbor Laboratory Press, USA, 1989). For example, a cDNA library derived from a specific Eimeria strain is transferred, or "blotted" onto a piece of nitrocellulose filter. It is now possible to identify specific Eimeria nucleic acid sequences on the filter by hybridization to a defined labeled DNA fragment or "probe", i.e. a (synthetic) poly- or oligonucleotide sequence derived from the nucleic acid sequence shown in SEQ ID NO's: 1, 3, 5, 7 and 9, which under specific conditions of salt concentration and temperature hybridizes to the homologous nucleic acid sequences present on the filter. After washing the filter, hybridized material may be detected by autoradiography. The corresponding DNA fragment can now be eluted from the agarose gel and used to direct the synthesis of a functional variant of the polypeptide disclosed in SEQ ID NO's: 2, 4, 6, 8 or 10.

Typically, a cDNA library from Eimeria can be constructed exactly according to the procedure described in Example 3. The inserts from clones pGEM4Z Eam200, pGEM4Z Eam45 M1(E), pGEM4Z Eam45 M3(E) pGEM4Z Eam20(E) or pGEM4Z Eam100E can be labeled with digoxigenin-dUTP by random priming, exactly following the protocol going with the "DNA labelling and detection kit, non-radioactive" from Boehringer, Mannheim (Cat. No. 1093657).

Filters containing immobilized DNA from the Eimeria cDNA library described above can be prepared as described by Maniatis et al., supra and probed by the freshly denatured (10 min. 95° C.), labeled Eimeria fragment for 16 hours at 42° C. according to the manufacturer's instructions. Filters are then washed as follows: twice for fifteen minutes with 2×SSC, 0.1% (w/v) SDS (1×SSC is 0.015 mol/l sodium citrate pH 7.0 plus 0.15 mol/l NaCl) at room temperature and twice for fifteen minutes with 1×SSC, 0.1% (w/v) SDS at 55° C. For final identification filters are then washed twice with PBS-tween (7.65 g/l NaCl, 0.91 g/l Na$_2$HPO$_4$.2H$_2$O, 0.21 g/l KH$_2$PO$_4$, 0.05% (v/v) Tween 80, pH 7.3) for 15 minutes at room temperature. The filters were then reacted with a 1:5000 dilution in PBS-tween of polyclonal sheep anti-digoxigenin Fab-fragments, conjugated to alkaline phosphatase, for thirty minutes at room temperature. After washing the filters for four times fifteen minutes with PBS-tween at room temperature and once for fifteen minutes with 0.01M Tris-HCl pH 8.0, 0.15M NaCl, binding of the alkaline phosphatase to the filters was detected upon incubation with a solution of 0.33 g/l Nitroblue tetrazolium and 0.17 g/l 5-bromo-4-chloro-3-indolylphosphate in 0.1M Tris-HCl pH 9.6, 0.1M NaCl, 0.01M MgCl$_2$. The DNA that reacts with the probe can be used to express the encoding polypeptide as outlined below.

Thereafter, the polypeptide can be assayed for the presence of one or more immunogenic determinants of an Eimeria antigen protein according to one of the following methods.

The polypeptide can be purified from the E.coli lysate by methods known in the art, such as salt fractionation, ionic exchange chromatography, hydrophobic interaction chromatography, or metal chelate chromatography. The purified product can be used to raise monospecific antibodies as described below. The antibodies can be probed back onto Western blots of parasite material such as merozoites or sporozoites. Positive signals connect the product of the E.coli translation directly to the parasite protein.

Another possibility to achieve this is the anti-body select technique binding antibodies directly to a filter containing a monoculture of recombinant phages in E.coli expressing the Eimeria DNA insert. By eluting these bound antibodies using the procedure of Osaki et al (J. Immunological Methods 89, 213–219, 1986) and allowing them to bind again to Western blots of Eimeria antigens the connection is a fact. The latter procedure was followed for the Eas100 and the Eam45 clones (Example 3, FIGS. 8 and 9).

The hybridization techniques described above may also be used in order to arrive at full length clones in case only a portion of the total coding sequence has been identified. In particular clone pGEM4Z Eam200 and pGEM4Z Eam100E may be used to screen cDNA or genomic DNA libraries for possible additional coding sequence.
Another method to extend DNA sequences is the "semi-specific" polymerase chain reaction outlined in Example 3.

Therefore, a nucleic acid sequence encoding a functional variant of the proteins disclosed herein encodes a polypeptide comprising one or more immunogenic determinants of an Eimeria antigen and hybridizes to the DNA sequence shown in SEQ ID NO's: 1, 3, 5, 7 or 9.

In another way Eimeria cDNA may be cloned into a λgt11 phage as described by Huynh et al. (In: D. Glover (ed.), DNA Cloning: A Practical Approach, IRL Press Oxford, 49–78, 1985) and expressed into a bacterial host. Recombinant phages can then be screened with polyclonal serum raised against the purified Eimeria proteins described above or in SEQ ID NO's: 2, 4, 6, 8 or 10 determining the presence of corresponding immunological regions of the variant polypeptide. The production of the polyclonal serum to be used herein elicited against the Eimeria proteins is described below.

More particularly, the present invention comprises nucleic acid sequences encoding a protein having one or more immunogenic determinants of an Eimeria antigen, wherein the nucleic acid sequences contain at least part of the DNA sequences shown in SEQ ID NO's: 1, 3, 5, 7 or 9, respectively.

A nucleic acid sequence according to the invention may be isolated from a particular Eimeria strain and multiplied by recombinant DNA techniques including polymerase chain reaction (PCR) technology or may be chemically synthesized in vitro by techniques known in the art.

A nucleic acid sequence according to the present invention can be ligated to various replication effecting DNA sequences with which it is not associated or linked in nature resulting in a so called recombinant vector molecule which can be used for the transformation of a suitable host. Useful recombinant vector molecules, are preferably derived from, for example plasmids, bacteriophages, cosmids or viruses.

Specific vectors or cloning vehicles which can be used to clone nucleic acid sequences according to the invention are known in the art and include inter alia plasmid vectors such as pBR322, the various pUC, pGEM and Bluescript plasmids, bacteriophages, e.g. λgt-Wes, Charon 28 and the M13 derived phages or viral vectors such as SV40, adenovirus or polyoma virus (see also Rodriquez, R. L. and D. T. Denhardt, ed., Vectors: A survey of molecular cloning vectors and their uses, Butterworths, 1988; Lenstra, J. A. et al., Arch. Virol. 110, 1–24, 1990). The methods to be used for the construction of a recombinant vector molecule according to the invention are known to those of ordinarily skill in the art and are inter alia set forth in Maniatis, T. et al. (Molecular Cloning A Laboratory Manual, second edition; Cold Spring Harbor Laboratory, 1989).

For example, the insertion of the nucleic acid sequence according to the invention into a cloning vector can easily be achieved when both the genes and the desired cloning vehicle have been cut with the same restriction enzyme(s) as complementary DNA termini are thereby produced.

Alternatively, it may be necessary to modify the restriction sites that are produced into blunt ends either by digesting the single-stranded DNA or by filling in the single-stranded termini with an appropriate DNA polymerase. Subsequently, blunt end ligation with an enzyme such as T4 DNA ligase may be carried out.

If desired, any restriction site may be produced by ligating linkers onto the DNA termini. Such linkers may comprise specific oligonucleotide sequences that encode restriction site sequences. The restriction enzyme cleaved vector and nucleic acid sequence may also be modified by homopolymeric tailing.

"Transformation", as used herein, refers to the introduction of a heterologous nucleic acid sequence into a host cell, irrespective of the method used, for example direct uptake or transduction. The heterologous nucleic acid sequence may be maintained through autonomous replication or alternatively, may be integrated into the host genome. If desired, the recombinant vector molecules are provided with appropriate control sequences compatible with the designated host which can regulate the expression of the inserted nucleic acid sequence. In addition to microorganisms, cell cultures derived from multi-cellular organisms may also be used as hosts.

The recombinant vector molecules according to the invention preferably contain one or more marker activities that may be used to select for desired transformants, such as ampicillin and tetracycline resistance in pBR322, ampicillin resistance and α-peptide of β-galactosidase in pUC8.

A suitable host cell is a microorganism or cell which can be transformed by a nucleic acid sequence encoding a polypeptide or by a recombinant vector molecule comprising such a nucleic acid sequence and which can if desired be used to express said polypeptide encoded by said nucleic acid sequence. The host cell can be of procaryotic origin, e.g. bacteria such as *Escherichia coli, Bacillus subtilis* and *Pseudomonas* species; or of eucaryotic origin such as yeasts, e.g. *Saccharomyces cerevisiae* or higher eucaryotic cells such as insect, plant or mammalian cells, including HeLa cells and Chinese hamster ovary (CHO) cells. Insect cells include the Sf9 cell line of *Spodoptera frugiperda* (Luckow et al., Bio-technology 6, 47–55, 1988). Information with respect to the cloning and expression of the nucleic acid sequence of the present invention in eucaryotic cloning systems can be found in Esser, K. et al. (Plasmids of Eukaryotes, Springer-Verlag, 1986).

In general, prokaryotes are preferred for the construction of the recombinant vector molecules useful in the invention. For example *E.coli* K12 strains are particularly useful such as DH5α or MC1061λ.

For expression nucleic acid sequences of the present invention are introduced into an expression vector, i.e. said sequences are operably linked to expression control sequences. Such control sequences may comprise promoters, enhancers, operators, inducers, ribosome binding sites etc. Therefore, the present invention provides a recombinant vector molecule comprising a nucleic acid sequence encoding an Eimeria protein identified above operably linked to expression control sequences, capable of expressing the DNA sequences contained therein in (a) transformed host cell(s).

It should, of course, be understood that the nucleotide sequences inserted at the selected site of the cloning vector may include nucleotides which are not part of the actual structural gene for the desired polypeptide or may include only a fragment of the complete structural gene for the desired protein as long as transformed host will produce a polypeptide having at least one or more immunogenic determinants of an Eimeria antigen.

When the host cells are bacteria, illustrative useful expression control sequences include the Trp promoter and operator (Goeddel, et al., Nucl. Acids Res. 8, 4057, 1980); the lac promoter and operator (Chang, et al., Nature 275, 615, 1978); the outer membrane protein promoter (Nakamura, K. and Inouge, M., EMBO J. 1, 771–775, 1982); the bacteriophage promoters and operators (Remaut, E. et al., Nucl. Acids Res. 11, 4677–4688, 1983); the α-amylase (B. subtilis) promoter and operator, termination sequence and other expression enhancement and control sequences compatible with the selected host cell. When the host cell is yeast, illustrative useful expression control sequences include, e.g., α-mating factor. For insect cells the polyhedrin or p10 promoters of baculoviruses can be used (Smith, G. E. et al., Mol. Cell. Biol. 3, 2156–65, 1983). When the host cell is of mammalian origin illustrative useful expression control sequences include, e.g., the SV-40 promoter (Berman, P. W. et al., Science 222, 524–527, 1983) or, e.g. the metallothionein promoter (Brinster, R. L., Nature 296, 39–42, 1982) or a heat shock promoter (Voellmy et al., Proc. Natl. Acad. Sci. USA 82, 4949–53, 1985). Alternatively, also expression control sequences present in Eimeria may be applied. For maximizing gene expression, see also Roberts and Lauer (Methods in Enzymology 68, 473, 1979).

Therefore, the invention also comprises (a) host cell(s) transformed with a nucleic acid sequence or recombinant expression vector molecule described above, capable of producing the Eimeria protein by expression of the nucleic acid sequence.

Immunization of avians against Eimeria infection can, for example be achieved by administering to the animals a protein according to the invention in an immunologically relevant context as a so-called subunit vaccine. The subunit vaccine according to the invention may comprise a protein in a pure form, optionally in the presence of a pharmaceutically acceptable carrier. The protein can optionally be covalently bonded to a non-related protein, which, for example can be of advantage in the purification of the fusion product. Examples are β-galactosidase, protein A, prochymosine, blood clotting factor Xa, etc.

In some cases the ability to raise protective immunity using these proteins per se may be low. Small fragments are preferably conjugated to carrier molecules in order to raise their immunogenicity. Suitable carriers for this purpose are macromolecules, such as natural polymers (proteins like key hole limpet hemocyanin, albumin, toxins), synthetic polymers like polyamino acids (polylysine, poly-alanine), or micelles of amphiphilic compounds like saponins. Alternatively these fragments may be provided as polymers thereof, preferably linear polymers.

Proteins to be used in such subunit vaccines can be prepared by methods known in the art, e.g. by isolating said polypeptides from Eimeria parasites, by recombinant DNA techniques or by chemical synthesis.

If required the proteins according to the invention to be used in a vaccine can be modified in vitro or in vivo, for example by glycosylation, amidation, carboxylation or phosphorylation.

An alternative to subunit vaccines are live vector vaccines. A nucleic acid sequence according to the invention is introduced by recombinant DNA techniques into a micro-organism (e.g. a bacterium or virus) in such a way that the recombinant micro-organism is still able to replicate thereby expressing a polypeptide coded by the inserted nucleic acid sequence and eliciting an immune response in the infected host animal.

A preferred embodiment of the present invention is a recombinant vector virus comprising a heterologous nucleic acid sequence described above, capable of expressing the DNA sequence in (a) host cell(s) or host animal infected with the recombinant vector virus. The term "heterologous" indicates that the nucleic acid sequence according to the invention is not normally present in nature in the vector virus.

Furthermore, the invention also comprises (a) host cell(s) or cell culture infected with the recombinant vector virus, capable of producing the Eimeria protein by expression of the nucleic acid sequence.

For example the well known technique of in vivo homologous recombination can be used to introduce a heterologous nucleic acid sequence, e.g. a nucleic acid sequence according to the invention into the genome of the vector virus.

First, a DNA fragment corresponding with an insertion region of the vector genome, i.e. a region which can be used for the incorporation of a heterologous sequence without disrupting essential functions of the vector such as those necessary for infection or replication, is inserted into a cloning vector according to standard recDNA techniques. Insertion-regions have been reported for a large number of micro-organisms (e.g. EP 80,806, EP 110,385, EP 83,286, EP 314,569, WO 88/02022, WO 88/07088, U.S. Pat. No. 4,769,330 and U.S. Pat. No. 4,722,848).

Second, if desired, a deletion can be introduced into the insertion region present in the recombinant vector molecule obtained from the first step. This can be achieved for example by appropriate exonuclease III digestion or restriction enzyme treatment of the recombinant vector molecule from the first step.

Third, the heterologous nucleic acid sequence is inserted into the insertion-region present in the recombinant vector molecule of the first step or in place of the DNA deleted from said recombinant vector molecule. The insertion region DNA sequence should be of appropriate length as to allow homologous recombination with the vector genome to occur. Thereafter, suitable cells can be infected with wild-type vector virus or transformed with vector genomic DNA in the presence of the recombinant vector molecule containing the insertion flanked by appropriate vector DNA sequences whereby recombination occurs between the corresponding regions in the recombinant vector molecule and the vector genome. Recombinant vector progeney can now be produced in cell culture and can be selected for example genotypically or phenotypically, e.g. by hybridization, detecting enzyme activity encoded by a gene co-integrated along with the heterologous nucleic acid sequence, or detecting the antigenic heterologous polypeptide expressed by the recombinant vector immunologically.

Next, this recombinant micro-organism can be administered to poultry for immunization whereafter it maintains itself for some time, or even replicates in the body of the inoculated animal, expressing in vivo a polypeptide coded for by the inserted nucleic acid sequence according to the invention resulting in the stimulation of the immune system of the inoculated animal. Suitable vectors for the incorporation of a nucleic acid sequence according to the invention can be derived from viruses such as pox viruses, e.g. vaccinia virus (EP 110,385, EP 83,286, U.S. Pat. No. 4,769, 330 and U.S. Pat. No. 4,722,848) or fowl pox virus (WO 88/02022), herpes viruses such as HVT (WO 88/07088) or Marek's Disease virus, adeno virus or influenza virus, or bacteria such as *E. coli* or specific Salmonella species. With recombinant microorganisms of this type, the polypeptide synthesized in the host animal can be exposed as a surface antigen. In this context fusion of the said polypeptide with OMP proteins, or pilus proteins of for example *E. coli* or synthetic provision of signal and anchor sequences which are recognized by the organism are conceivable. It is also possible that the said immunogenic polpeptide, if desired as part of a larger whole, is released inside the animal to be immunized. In all of these cases it is also possible that one or more immunogenic products will find expression which generate protection against various pathogens and/or against various antigens of a given pathogen.

A vector vaccine according to the invention can be prepared by culturing a recombinant bacterium or a host cell infected with a recombinant vector virus comprising a nucleic acid sequence according to the invention, whereafter recombinant bacteria or virus containing cells and/or recombinant vector viruses grown in the cells can be collected, optionally in a pure form, and formed to a vaccine optionally in a lyophilized form.

Host cells transformed with a recombinant vector molecule according to the invention can also be cultured under conditions which are favourable for the expression of a polypeptide coded by said nucleic acid sequence. Vaccines may be prepared using samples of the crude culture, host cell lysates or host cell extracts, although in another embodiment more purified polypeptides according to the invention are formed to a vaccine, depending on its intended use. In order to purify the polypeptides produced, host cells transformed with a recombinant vector according to the invention are cultured in an adequate volume and the polypeptides produced are isolated from such cells or from the medium if the protein is excreted. Polypeptides excreted into the medium can be isolated and purified by standard techniques, e.g. salt fractionation, centrifugation, ultrafiltration, chromatography, gel filtration or immuno affinity chromatography, whereas intra cellular polypeptides can be isolated by first collecting said cells, disrupting the cells, for example by sonication or by other mechanically disruptive means such as French press followed by separation of the polypeptides from the other intra cellular components and forming the polypeptides to a vaccine. Cell disruption could also be accomplished by chemical (e.g. EDTA or detergents such as Triton X114) or enzymatic means such as lysozyme digestion.

Antibodies or antiserum directed against a polypeptide according to the invention have potential use in passive immunotherapy, diagnostic immunoassay's and generation of anti-idiotype antibodies.

The Eimeria proteins as characterized above can be used to produce antibodies, both polyclonal, monospecific and monoclonal. If polyclonal antibodies are desired techniques for producing and processing polyclonal sera are known in the art (e.g. Mayer and Walter, eds, Immunochemical Methods in Cell and Molecular Biology, Academic Press, London, 1987). In short, a selected mammal, e.g. rabbit is given (multiple) injections with above-mentioned immunogens, about 20 μg to about 80 μg of protein per immunization. Immunizations are given with an acceptable adjuvant, generally equal volumes of immunogen and adjuvant. Acceptable adjuvants include Freund's complete, Freund's incomplete, alum-precipitate or water-in-oil emulsions, with Freund's complete adjuvant being preferred for the initial immunization. Freund's incomplete adjuvant is preferred for all booster immunizations. The initial immunization consists of the administration of about 1 ml of emulsion at multiple subcutaneous sites on the backs of the rabbits. Booster immunizations utilizing an equal volume of immunogen are given at about one month intervals and are continued until adequate levels of antibodies are present in an individual rabbits serum. Blood is collected and serum isolated by methods known in the art.

Monospecific antibodies to the immunogen are affinity purified from polyspecific antisera by a modification of the method of Hall et al. (Nature 311, 379–387 1984), prepared by immunizing rabbits as described above with the purified proteins. Monospecific antibody as used herein is defined as a single antibody species or multiple antibody species with homogeneous binding characteristics for the relevant antigen. Homogeneous binding as used herein refers to the ability of the antibody species to bind to a specific antigen or epitope.

Monoclonal antibody reactive against the Eimeria immunogens can be prepared by immunizing inbred mice, preferably Balb/c with the appropriate protein. The mice are immunized intraperitoneally with about 100 ng to about 10 μg immunogen per 0.5 ml dose in an equal volume of an acceptable adjuvant. Such acceptable adjuvants include Freund's complete, Freund's incomplete, alum-precipitate and water-in-oil emulsions. The mice are given intravenous booster immunizations of an equal amount of the immunogen without adjuvant at about days 14, 21 and 63 post primary immunization. At about day three after the final booster immunization individual mice are serologically tested for anti-immunogen antibodies. Spleen cells from antibody producing mice are isolated and fused with murine myeloma cells, such as SP-2/0 or the like, by techniques known in the art (Kohler and Milstein, Nature 256; 495–497, 1975). Hybridoma cells are selected by growth in hypoxanthine, thymidine and aminopterin in an appropriate cell culture medium such as Dulbecco's modified Eagle's medium (DMEM). Antibody producing hybridomas are cloned, preferably using the soft agar technique of MacPherson, (Soft Agar Techniques, Tissue Culture Methods and Applications, Kruse and Paterson, eds., Academic Press, 276, 1973). Discrete colonies are transferred into individual wells of culture plates for cultivation in an appropriate culture medium. Antibody producing cells are identified by screening with the appropriate immunogen. Immunogen positive hybridoma cells are maintained by techniques known in the art. Specific anti-monoclonal antibodies are produced by cultivating the hybridomas in vitro or preparing ascites fluid in mice following hybridoma injection by procedures known in the art.

Anti-idiotype antibodies are immunoglobulins which carry an "internal image" of the antigen of the pathogen against which protection is desired and can be used as an immunogen in a vaccine (Dreesman et al., J. Infect. Disease 151, 761, 1985). Techniques for raising anti-idiotype antibodies are known in the art (MacNamara et al., Science 226, 1325, 1984).

The vaccine according to the invention can be administered in a convential active immunization scheme: single or repeated administration in a manner compatible with the dosage formulation and in such amount as will be prophylactically effective, i.e. the amount of immunizing antigen or recombinant micro-organism capable of expressing said antigen that will induce immunity in avians against challenge by virulent Eimeria parasites. Immunity is defined as the induction of a significant level of protection in a population of chickens after vaccination compared to an unvaccinated group.

For live vital vector vaccines the dose rate per chicken may range from $10^5-10^8$ pfu.

A typical subunit vaccine according to the invention comprises 1 µg-1 mg of the protein according to the invention.

The administration of the vaccine can be done, e.g. intradermally, subcutaneously, intramuscularly, intraperitoneally, intravenously, orally or intranasally.

Additionally the vaccine may also contain an aqueous medium or a water containing suspension, often mixed with other constituents, e.g. in order to increase the activity and/or shelf life. These constituents may be salts, pH buffers, stabilizers (such as skimmed milk or casein hydrolysate), emulsifiers adjuvants to improve the immune response (e.g. oils, muramyl dipeptide, aluminiumhydroxide, saponin, polyanions and amphipatic substances) and preservatives.

It is clear that a vaccine according to the invention may also contain immunogens related to other pathogens of poultry or may contain nucleic acid sequences encoding these immunogens, like antigens of Marek's Disease virus (MDV), Newcastle Disease virus (NDV), Infectious Bronchitis virus (IBV), Infectious Bursal Disease virus (IBDV), Chicken Anemia Agent (CAA), Reo virus, Avian Retro virus, Fowl Adeno virus, Turkey Rhinotracheitis virus, $E.$ $coli$ or other Eimeria species to produce a multivalent vaccine.

The invention also relates to an "immunochemical reagent", which reagent comprises a protein according to the invention.

The term "immunochemical reagent" signifies that the protein according to the invention is bound to a suitable support or is provided with a labelling substance.

The supports which can be used are, for example, the inner wall of a microtest well or a cuvette, a tube or capillary, a membrane, filter, test strip or the surface of a particle such as, for example, a latex particle, an erythrocyte, a dye sol, a metal sol or metal compound as sol particle.

Labelling substances which can be used are, inter alia, a radioactive isotope, a fluorescent compound, an enzyme, a dye sol, metal sol or metal compound as sol particle.

A nucleic acid sequence according to the invention can also be used to design specific probes for hybridization experiments for the detection of Eimeria related nucleic acids in any kind of tissue.

The present invention also comprises a test kit comprising said nucleic acid sequence useful for the diagnosis of Eimeria infection.

The invention also relates to a test kit to be used in an immuno-assay, this test kit containing at least one immunochemical reagent according to the invention.

The immunochemical reaction which takes place using this test kit is preferably a sandwich reaction, an agglutination reaction, a competition reaction or an inhibition reaction.

For carrying out a sandwich reaction, the test kit can consist, for example, of a polypeptide according to the invention bonded to a solid support, for example the inner wall of a microtest well, and either a labelled polypeptide according to the invention or a labelled anti-antibody.

EXAMPLE 1

Preparation and Isolation of Parasites $E.acervulina$ Houghton strain was obtained from the AFRC Houghton Laboratory and was passaged through coccidia-free chickens.

Preparation of parasites and fractions thereof $E.$ $tenella$ parasites were maintained and oocysts were isolated according to methods described by Long et al. (Fol. Vet. Lat. 6, 201–217, 1976). Sporozoites were isolated and purified as described by Wisher & Rose (Parasitology 88, 515–519, 1984) with an additional nylon wool purification as described by Larsen, et al. (J.Parasitol. 70, 597–601, 1984).

Merozoites were harvested at 72 hours after inoculation as follows (see also Jenkins and Dame, Mol. Biochem. Parasitol. 25, 155–164, 1987): Four to six week old chickens were orally infected with $1-5\times 10^6$ sporulated oocysts. 72 hrs after inoculation the birds were killed and the duodenum was removed until the Meckels diverticulum and kept in icecold phosphate buffered saline (0.04M PBS pH 7.3). The duodenum was cut lengthwise and washed with icecold PBS. The gut was then cut into 5 cm pieces and suspended in Hanks-BSS containing 100–200 U/ml penicillin, 100–200 µg streptomycin/ml at 37° C. for 15–30 min.

The supernate was removed and filtered through 120, 60 and 35 mesh stainless steel sieves. The eluate was centrifuged at 130 g for 8 min. The supernates were collected and merozoites concentrated after centrifugation at 1500 g for 10 min at 4° C.

The concentrated pellets were resuspended in 25 mM Tris-HCl pH 8.0 containing 150 mM NaCl and purified over DE-52 (Whatman) equilibrated in the same buffer. The merozoites were eluting in the non-bound fraction. Yield about $1\times 10^9$ merozoites per infected chicken.

EXAMPLE 2

Purification of Eimeria Antigens

A. Methods

Triton X114 Extraction

According to Bordier (Bordier, C., J. Biol. Chem. 256, 1604–1607, 1981) materials:

precondensed Triton X114 (TX114) (see below), 10 mM Tris/HCl-150 mM NaCl pH 7.4 (TBS), 100 mM PhenylMethylSulfonylFluoride (PMSF) in isopropanol, 6% sucrose solution in TBS containing 0.06% TX114 (sucrose cushion).

$5\times 10^8$ $E.$ $acervulina$ merozoites were homogenized per ml of TBS. The mixture was made up to 1 mM PMSF and 10% (v/v) precondensed TX114.

Using mechanical shearing proteins were extracted for at least 2 hours at 0° C. Non-solubilised material was pelleted by centrifugation for 10' at 12,000 g at 4° C. in Eppendorf centrifuge. The supernatant containing solubilised material was layered onto an equal volume of sucrose cushion and incubated at 40° C. for 10 min.

After centrifugation for 10' at 400 g (ambient temperature), the topphase containing hydrophilic material was taken off and extracted once more, layered again on the same sucrose cushion and centrifuged as above.

The combined bottom fraction was kept separate from the remaining topfraction.

If waterphase needed to be completely undone from hydrophobic material the extraction was repeated once more.

All fractions were kept frozen at −70° C. until further analysis.

Precondensation of Triton X114

20 ml Triton X114 (Serva) was made up to 1 liter with cold TBS pH 7.4 mixed and incubated at 0°–4° C. After complete solubilization the solution was transferred to a 40° C. waterbath. Phase separation was complete after 16 hours. Topphase was removed and replaced by an equal volume of TBS. This procedure was repeated twice. The final bottom phase, called "precondensed TX114", was kept in 100 ml bottle at 4° C. The final TX114 concentration is approximately 20%.

Monoclonal Antibodies

Antibodies were raised in Balb/C mice against *E.acervulina* merozoites by repeated intraperitoneal inoculations with $10^6$–$10^7$ merozoites.

The respective spleen cells were fused with myeloma P3X63Ag 8.6.5.3. and cloned as described by Schönherr et al. (Develop. biol. Stand. 50, 235–242, 1982).

Screenings were done by an immunofluorescence test on dried, acetone-fixed, merozoites. Highly concentrated monoclonal antibody solutions were prepared in vitro using dialysis modules as culture vessels with continuous medium replacement as described by Schönherr and van Gelder (Animall Cell Biotechnology 3, 337–355).

Immuno-affinity chromatography

Activation of affinity matrix

Sepharose CL-4B (Pharmacia) was activated using Cyanogen Bromide (CNBr) 50 mg/ml in distilled water. Activation was carried out in a well ventilated hood. The mixture was stirred with a slowly turning magnetic bar and pH was kept on 10.5–11.0 with 4M NaOH for ±30 min. at ambient temperature. After the reaction had completed the sepharose was washed on a glass-sintered filter with 500 ml cold water and 500 ml cold 0.2M NaHCO$_3$ (coupling buffer). The gel was used immediately for coupling the immunoglobulins.

Coupling of monoclonal IgG to Sepharose

Monoclonal antibody was used as highly concentrated supernatant but dialysed extensively against 0.2M NaHCO$_3$ (coupling buffer). Buffer exchange was also done using PD10 columns (Pharmacia) according to the manufacturers protocol. The CNBr-activated sepharose-CL-4B was made up to 2–5 mg/ml MoAb IgG, final concentration and the mixture was stirred end-over-end overnight at 4° C. or 2 hours on ambient temperature. The non-bound fraction was removed and assayed for protein using BCA reagent (Pierce). The Sepharose was washed ten times and subsequently mixed with 1 volume 1M ethanolamine/HCl pH 8.5 end-over-end for 2 hours at ambient temperature. By subsequent washing with four alternating cycles of 200 ml 0.1M Tris/HCl −0.5M NaCl pH 8.0 and 0.1M HAc-0.5M NaCl pH 4.0 non-covalently bound material was removed. The gel was stored at +4° C. in PBS 0.05% azide.

Affinity Purification

Buffers

A) 25 mM Tris/HCl+0.5M NaCl+0.1% Nonidet P40 (NP40) pH 8.0

B) 0.1M glycine/HCl+0.1% NP40 pH 2.6

C) 0.1M Tris/HCl+0.5M NaCl+0.1% NP40 pH 8.0

D) 3M KSCN in A)

E) 1M Tris/HCl pH 8.0

F) 10 mM Tris/HCl+150 mM NaCl pH 8.0

7 ml Sepharose-IgG was transferred to a Pharmacia C10/20 column equipped with cooling jacket. Ten times diluted TX114 hydrophobic extract (pellet) in buffer A was applied to the column at 0.5 ml/min. and recirculated for 16–20 hours at 8° C. After washing the column with 5–10 bedvolumes of buffer A), direction of flow was inverted followed by elution with 7.5 ml buffer B), 5 ml buffer C), 10 ml buffer A), 7.5 ml buffer D) and 40 ml buffer A).

Acidic fractions (1 ml) were neutralized immediately with 0.1 ml buffer E). KSCN fractions were dialysed overnight against buffer F). All fractions were analysed on SDS-PAGE, immunoblots and for protein contents by BCA assay. SDS-Polyacrylamide gel electrophoresis (SDS-PAGE) and immunoblotting SDS-PAGE was performed on 12% acrylamide gels using the Laemmli buffer system (Laemmli, U.K., Nature 227, 680–685, 1970). Western blotting was carried out according to Vermeulen et al (Vermeulen, A. N. et al., J. Exp. Med. 162, 1460–1476, 1985), using 25× diluted Laemmli lower vessel electrophoresis buffer as blot buffer. Blotting occurred for 1.5 hour at 90 V in a Bio-rad transblot cell.

Nitrocellulose (0.25 μm Schleicher and Schüll) was blocked with 0.1% NFMP (non-fat milk powder (OXOID)) in PBS (0.01M Phosphate in 0.9% saline pH 7.3) for 30 min.

Serum and alkaline phosphatase conjugated anti-serum (Zymed) were incubated for 1.5 hour. Positive binding was detected using BCIP/NBT as substrate.

Polyclonal antibodies

Rabbit 8275 (K8275) antibodies were raised in rabbits (New Zealand White) by immunisation with *E.acervulina* 72 hours merozoites in Freund-incomplete like adjuvant emulsion given intradermally twice with 4 weeks interval.

Monospecific antibodies were raised in rabbits previously selected for the absence of anti-Eimeria antibodies in the serum.

Rabbits 5706 and 5792 were injected twice (4–5 wks interval) with 55–100 μg affinity purified Eam45 emulsified with a Freund-incomplete-like (water in oil) adjuvant.

Rabbit 5796 was injected with affinity purified Eam20 according to the same protocol.

Rabbit 5794 was injected with the TX114 hydrophobic extract prior to affinity purification again using the same protocol. This fraction contained Eam45 and Eam20 and some other proteins.

Monospecific antibodies against Eas100 were raised in chickens using the purified protein in 100 mM Tris-HCL+150 mM NaCL+0.1% NP40 pH 8.0 emulsified in a Freund's incomplete like adjuvant administered three times subcutaneously in the neck with 14 days intervals. 11 days after the last immunization the chickens were bled and serum was collected (serum from chicken 323 was used for further studies).

B. RESULTS

TX114 extraction

Figure 3:
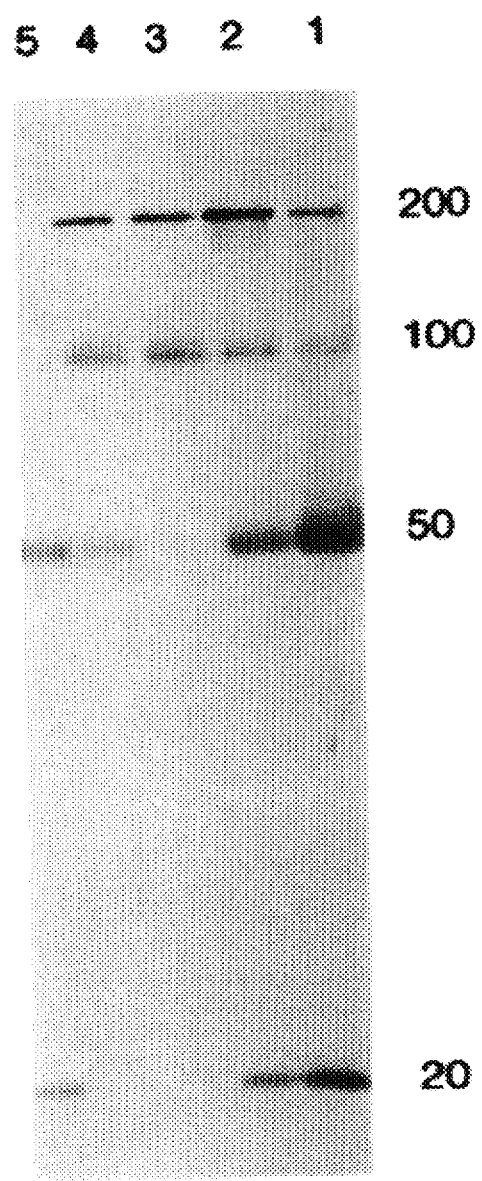
FIG. 3 is a Western blot of different fractions of TX114 extraction of *E. acervulina* merozoites.

FIG. 3 shows the different fractions obtained after TX114 extraction and phase separation. The material was electrophoresed, blotted onto nitrocellulose and probed with a mixture of monoclonal antibodies with specificity for the Eam200, Eam100, Eam45 and Eam20 proteins with respective relative molecular mass of 180–210 kD (mean 200 kD), 95–105 kD (mean 100 kD), 45–55 kD (mean 50 kD) and 18–22 kD (mean 20 kD) determined under non-reducing conditions.

It appeared that Eam200 and Eam100 proteins were of hydrophilic character since they were not present in the hydrophobic pellet (lane 5). Contrarily the Eam45 and Eam20 were absent in the hydrophilic fraction (lane 3).

Immuno-affinity chromatography of Eam45 and Eam20

Monoclonal antibody E.ACER 10C-2A was coupled to sepharose to bind the Eam45 protein, whereas E.ACER 10E-2 was used to bind Eam 20.

Coupling efficiency was over 90% for both MoAbs, leakage of MoAb from the column was minimal.

The "Eam20" column was connected with the "Eam45" column so that the non-bound fraction of the latter was able to bind to the former matrix. Both columns were eluted separately.

Figure 4:
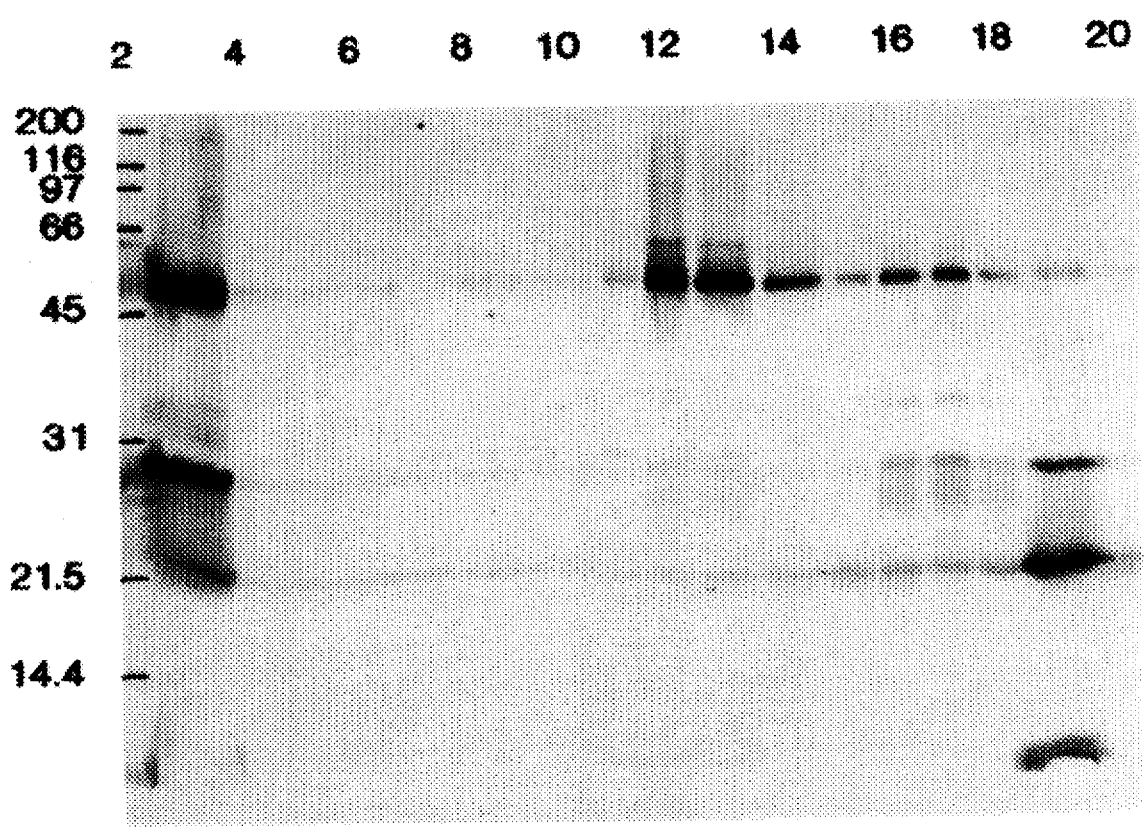
FIG. 4 is a Western blot of different fractions of immunoaffinity purification using E.ACER 10C-2A.

FIG. 4 shows the SDS-PAGE/Immuno blot of the fractions from the 10C-2A (Eam45) matrix. The figure was taken from an experiment different from FIG. 3. The blot was probed with rabbit K8275 antibodies. It appeared that the Eam45 predominantly eluted at pH 2.6 (lanes 12 to 14), although some remained, which eluted with the KSCN (lanes 16 to 18). The latter fractions, however, contained other lower molecular weight material probably not related to the Eam45 antigen.

Figure 5:
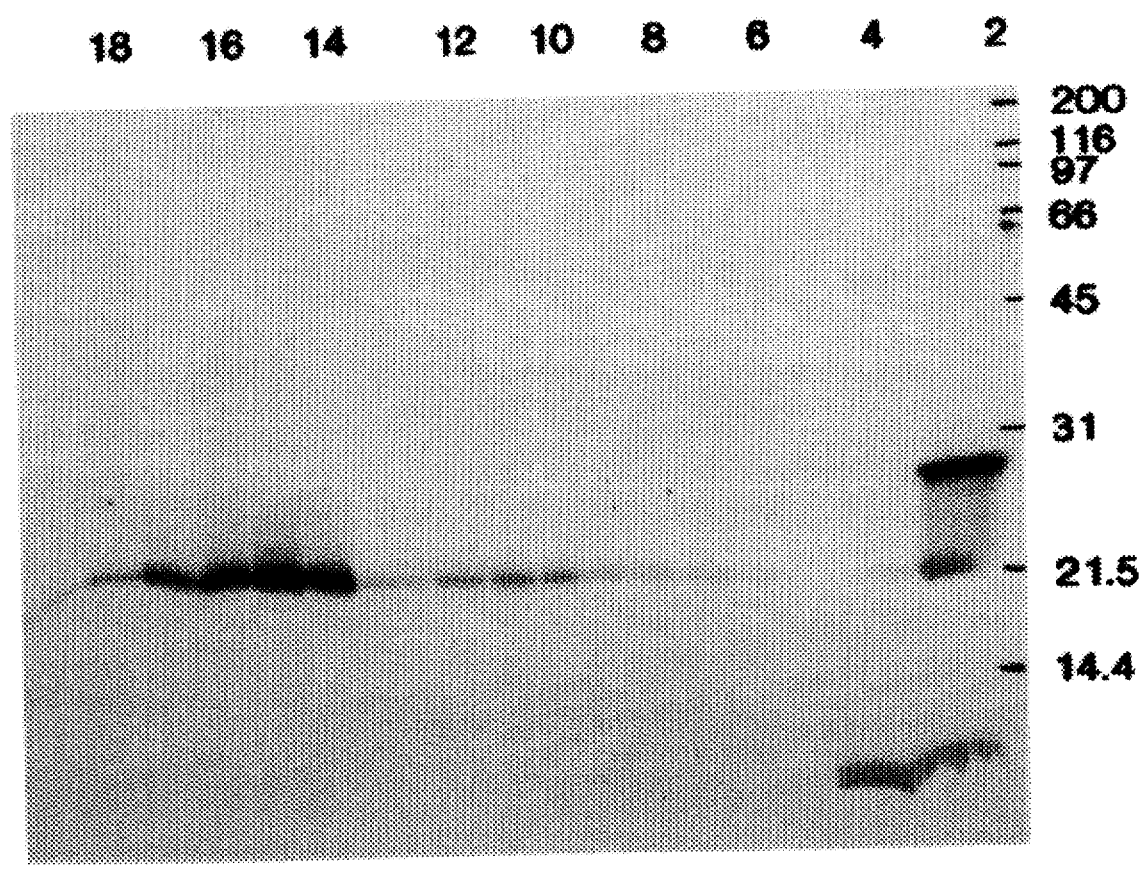
FIG. 5 is a Western blot of different fractions of immunoaffinity purification using E.ACER 10E-2.

FIG. 5 shows a similar blot but from the 10E-2 column binding the Eam20 material.

Lane 3 contained the material that did not bind to the 10C-2A column and was thus the starting material for the 10E-2 adsorbent. It appeared that this fraction did not contain any Eam45 material. The marked band at 29 kD was artefactual and belonged to the Eam20 protein. The artefact was induced by the presence of Triton X114 in the electrophoresis sample.

Lane 4 contained the non-bound fraction of the 10E-2 column, which demonstrated the high efficiency of this MoAb to absorb all Eam20 material.

Although some of the material eluted at pH 2.6 (lanes 10 to 12), the majority was released with 3M KSCN (lanes 14 to 17). These fractions did not contain any non-specifically bound material.

Monoclonals against both Eam45 and Eam20 recognized surface proteins on live merozoites.

The apparent MW of Eam45 as measure on SDS-PAGE was 45–55 kD but for reference to earlier reports it was decided not to change its identification. The MW of Eam45 is accorded about 50 kD herein. On reduced gels Eam45 runs at 55 kD.

All anti-Eam45 sera demonstrated positive reaction around 50 kD and 100 kD if these sera were used to probe back on merozoite blot.

Purification of *E. acervulina* 100 kD protein from sporozoites

For the purification of the *E.acervulina* 100 kD protein sporozoites were extracted with TX114 according to the protocol described above. The Eas100 was detected exclusively in the hydrophilic phase. This was subsequently allowed to bind to an immunoaffinity column of Moab E.ACER 5F-2 coupled to CNBr-activated-Sepharose-4B. Binding and elution conditions were as described above.

Figure 6:
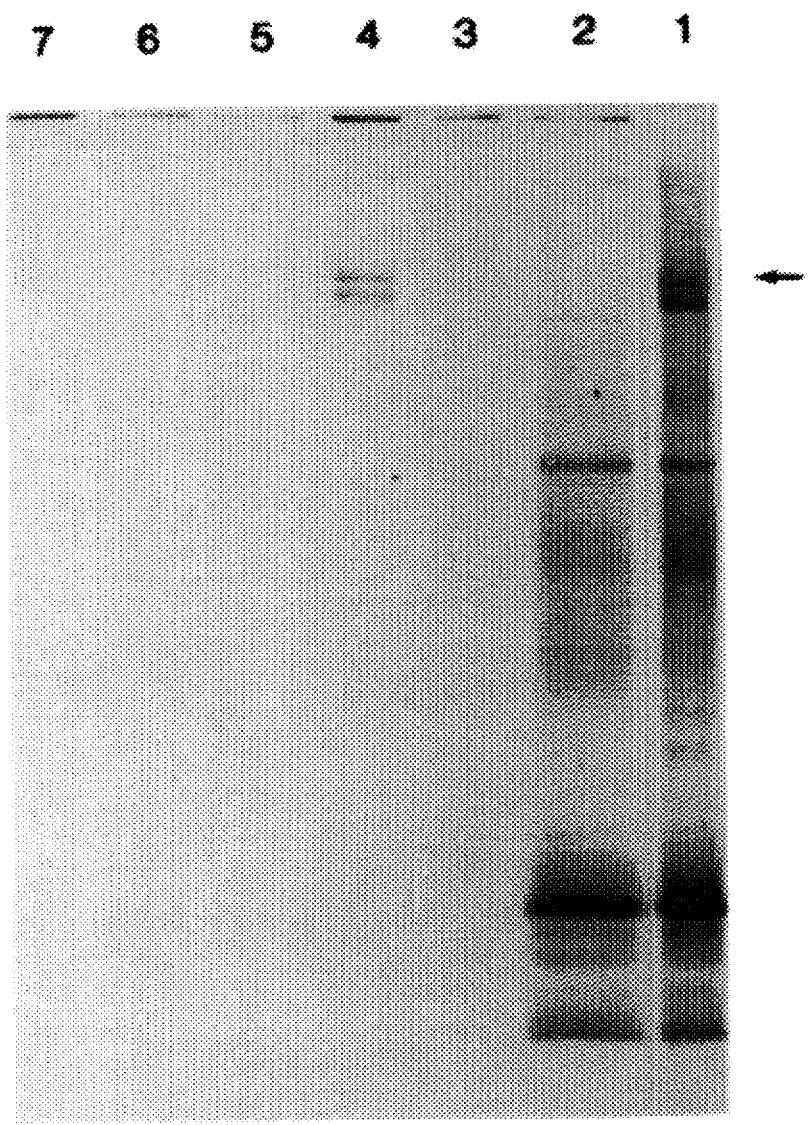
FIG. 6 is a Western blot of different fractions of immunoaffinity purification using E.ACER 5F-2.

The Eas100 eluted as a doublet at acidic pH. The fraction containing Eas100 is shown in FIG. 6 (lane 4). This blot was post-treated with rabbit anti-E.acer sporozoite antibodies.

No other parasite-derived bands were visible in this fraction. The only contaminating band (MW>200 kD) appeared to be caused by IgG leakage from the matrix.

This material was used to raise antibodies in chickens against Eas100.

Antibodies from chicken 323 were used to screen cDNA library derived from 72 hr *E.acervulina* merozoite mRNA (Example 3).

Ab-selected on the positive clone reacted against the Eas100 as expected and against a protein of similar size in *E.acervulina* merozoites. Immunoblotted affinity purified Eam100 (using MoAb E.ACER 16B-2B) reacted positively with E.ACER 5F-2, the MoAb that was used to purify the sporozoite equivalent Eas100. Therefore both proteins are related.

Immuno-affinity chromatography of Eam200 from merozoites

Monoclonal antibody E.ACER 11A-2A was coupled to sepharose to bind the Eam200 protein.

Coupling efficiency was over 90%, leakage of MoAb from the column was minimal, however detectable.

The hydrophilic fraction of the TX114 extraction containing Eam200 and Eam100 was allowed to bind to the column according to the protocol as described above for Eam45 and Eam20.

Figure 7:
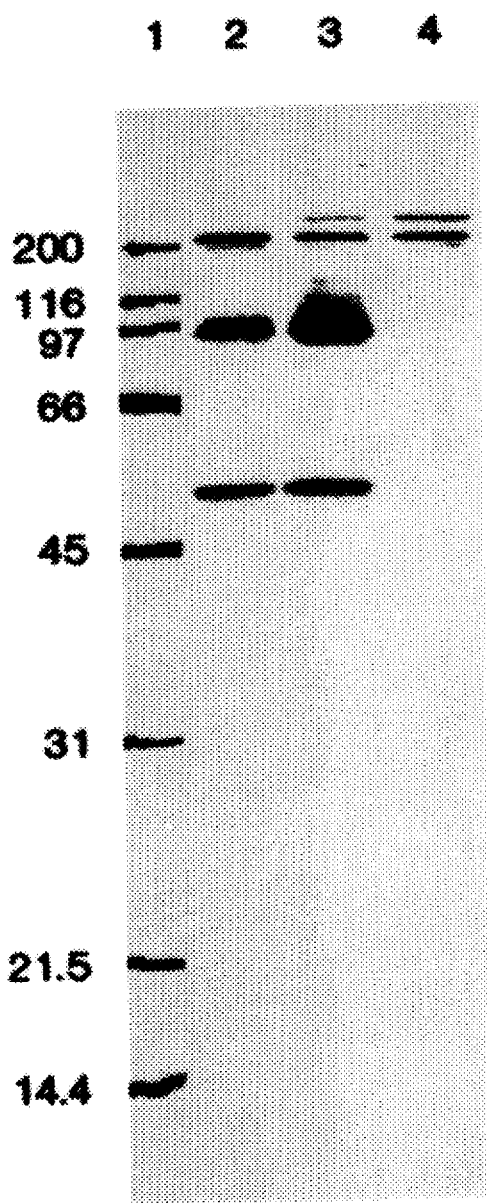
FIG. 7 is a Western blot of different fractions of immunoaffinity purification using E.ACER 11A-2A.

The purified Eam200 was released from the column after acidic elution as is shown in FIG. 7 (lane 4).

EXAMPLE 3

Preparation of cDNA Library of *E. acervulina* Merozoites, Immunological Screening and DNA Sequence Analysis A. Methods Isolation of RNA For the isolation of RNA a pellet of $10^9$ merozoites was resuspended in 0.5 ml $H_2O$. After addition of 0.5 ml solution A (Tris 10 mM, sodium acetate 75 mM, EDTA 2 mM, SDS 1% (pH 7.2)), 1 ml solution B (5M Guanidine-monoisothiocyanaat, EDTA 10 mM, Tris 50 mM (pH 7.5) and 2 g glassbeads (0.5 mm), the suspension was vortexed for 1 min. 4 ml solution B and 0.4 ml β-mercaptoethanol were added and the tubes placed in a waterbath (60° C.) for 15 minutes. After addition of 5 ml phenol the tubes were heated for another 15 minutes at 60° C. and cooled to room temperature (RT). The suspension was mixed by vortexing with 2.5 ml of (0.1M NaAc pH 5.2, 10 mM Tris (pH 7.5), 1 mM EDTA) and 5 ml chloroform-isoamylalcohol (24:1), after which the phases were separated by centrifugation (5 minutes at 6000 rpm). The waterphase was extracted once again with 20 ml phenol-chloroform-isoamylalcohol (25:24:1) by mixing for 10 minutes on a rollerdrum. After centrifugation for 5 minutes at 6000 rpm the nucleic acids were precipitated by addition of 2 volumes ethanol and collected by centrifugation (10 minutes at 6000 rpm). The pellet was washed with 70% ethanol and the poly $A^+$ RNA isolated as described by Maniatis et al. (Maniatis, T. et al., Molecular Cloning, A laboratory Manual, second edition, Cold Spring Harbor Laboratory Press, USA, 1989). Out of $10^9$ merozoites about 1 μg of poly $A^+$ RNA was isolated.

Construction of cDNA libraries

Poly $A^+$ RNA was converted to cDNA by means of the enzyme MMLV reverse transcriptase. For this purpose 0.5 μg poly $A^+$ mRNA was dissolved in 10 μl $H_2O$, heated for 10 minutes at 65° C. and then quickly cooled on ice. The cDNA synthesis was performed with the cDNA synthesis kit of Pharmacia. In order to obtain blunt-ended DNA molecules the cDNA was treated with 1 μl Klenow DNA Polymerase (7 U/μl) for 20 minutes at 37° C., followed by an incubation with 1 μl T4 DNA Polymerase (7.5 U/μl) for 10 minutes at 37° C. After extraction with an equal volume of phenol-chloroform-isoamylalcohol (25:24:1) and centrifugation (5 minutes at 13000 rpm, Biofuge), the cDNA was precipitated by the addition of 1 volume $NH_4Ac$ and 4 volumes ethanol. The pellet was washed with 70% ethanol and dissolved in 82 μl H$_2$O. EcoRI adaptors were ligated to the cDNA by addition of 10 μl ligationbuffer (Tris 500 mM (pH 8.0), MgCl$_2$ 100 mM, DTT 100 mM, ATP 100 mM and 50% (w/v) polypropyleneglycol 8000), 5 μl EcoRI adaptor solution (Pharmacia cDNA synthese kit) and 3 μl T4 DNA ligase (7 U/μl) and incubated overnight (O/N) at 12° C. The reaction was stopped by heating (10 minutes at 65° C.). The cDNA was phosphorylated by the addition of 10 μl ATP (10 mM) and 2 μl polynucleotide kinase (7 U/μl) and incubation for one hour at 37° C. The cDNA was extracted with 1 volume phenol-chloroform-isoamylalcohol (25:24:1) and purified on a Biogel A-15 m column. The cDNA containing fractions were precipitated by addition of 0.1 volume NaAc (3M NaAc (pH 5.6) and 2 volumes ethanol. The pellet was washed with 70% ethanol and dissolved in 20 μl T10E0.1 (Tris 10 mM (pH 7.6), EDTA 0.1 mM). The cDNA molecules were cloned in λgt10 or λgt11 DNA (according to Huynh et al. in: DNA cloning techniques: A practical approach, 1984).

Screening of lambda gt11 cDNA library with antisera against Eimeria proteins

The lambda gt11 cDNA library was screened with antibodies raised against proteins from Eimeria parasites. Either mouse monoclonal antibodies were used or monospecific rabbit or chicken antisera. Before use the antibodies were diluted in 1×Tris-salt (Tris-HCl 10 mM, NaCl 150 mM, pH 8.0)+0.05% Tween 20+10% Foetal Calf Serum (FCS) and incubated for 2 h at room temperature with the filters. The filters were then washed 4 times, for ten minutes each time, with 50 ml 1×Tris-salt+0.05% Tween 20 for each filter. For the second antibody incubation a conjugate of goat-anti-mouse or goat-anti-rabbit or rabbit-anti-chicken antibodies and alkaline phosphatase was used (diluted 1:7500 in 1×Tris salt+0.05% Tween 20+10% FCS) and incubated for 30 minutes at RT, after which the filters were washed as described above. The colour reaction was carried out in Tris-HCl 100 mM, NaCl 100 mM, MgCl$_2$ 10 mM (pH 9.6) in which 0.33 mg/ml Nitrobluetetrazolium and 0.17 mg/ml 5-Bromo-4-chloro-3-indolyl-phosphate had been dissolved. The reaction was stopped after 30 minutes incubation at room temperature.

Immunopositive clones were purified by two or three additional rounds of plating of isolated plaques and immunological screening as described above.

Characterization of lambda gt11 cDNA clones

Phage stocks were prepared and DNA extracted using standard techniques (Maniatis, T. et al., Molecular Cloning, A laboratory Manual, second edition, Cold Spring Harbor Laboratory Press, USA, 1989). After digestion with restriction endonucleases the DNA was analysed by electrophoresis on agarose gels in 89 mM Tris, 89 mM boric acid, 2 mM EDTA, pH 8.3.

Antibody select experiments were performed according to Osaki, L. S. et al. (J. Immunological Methods 89, 213–219, 1986) as a final proof for the identity of the proteins the isolated lambda gt11 cDNA clones are coding for. Phagestocks were diluted to 5×10$^4$ pfu/μl, 1 μl was incubated with 200 μl of cells of E.coli Y1090– and plated. After 2.5 h nitrocellulose filters saturated with IPTG were placed on the plates, after incubation for 5.5 h the filters were turned and the incubation proceeded for another 2 h. The plates with the filters were stored overnight at 4° C., after which the filters were washed with 1×Tris-salt for 20 minutes and blocked with 20% FCS in 1×Tris-salt for 2 h at room temperature. After a Tris-salt wash for 5 minutes at room temperature the filters were dried at the air. Antibody preparations were purified by caprilic acid precipitation and diluted 1:150 in 1×Tris-salt+20% FCS+0.05% NP40. Each filter was incubated with 15 ml of serum for 60 minutes at room temperature. The filters were washed 3× for 10 minutes with 1×Tris-salt+0.05% NP40. The bound IgG was eluted with 5 ml 0.2M Glycine-HCl (pH 2.8) for 1 minute at room temperature, quickly neutralized with 150 μl 2M Tris, 0.2 ml PBS Tween (25×) and 1 ml FCS (all dishes used for the elution steps were first blocked with 1×Tris-salt+10% FCS for 1 h at room temperature). The eluates were used on Western blot strips of Eimeria merozoites or sporozoites for identification of the corresponding proteins.

Screening of lambda gt10 cDNA library by hybridisation

The 200 bp insert from the lambda gt11/Eam 20 clone was labeled with digoxigenin-dUTP by random priming, exactly following the protocol going with the "DNA labeling and detection kit, non-radioactive" from Boehringer, Mannheim (Cat.no. 1093657). Filters containing immobilized DNA from the lambda gt10 E.acervulina cDNA library described above were prepared as described by Maniatis et al. (vide supra) and probed by the freshly denatured (10 min. at 95° C.) labeled E.acervulina cDNA fragment for 16 hours at 42° C. according to the manufacturers instructions. Filters were washed as follows: twice for fifteen minutes with 2×SSC, 0.1% (w/v) SDS (1×SSC is 0.015 mol/l sodium citrate pH 7.0 plus 0.15 mol/l NaCl) at room temperature, twice for fifteen minutes with 1×SSC, 0.1% (w/v) SDS at 60° C., twice for thirty and once for fifteen minutes with 0.1×SSC, 0.1% (w/v) SDS at 60° C. and twice with PBS-tween (7.65 g/l NaCl, 0.91 g/l Na$_2$HPO$_4$.2H$_2$O, 0.21 g/l KH$_2$PO$_4$, 0.05% (v/v) Tween 80, pH 7.3) for 15 minutes at room temperature.

The filters were then reacted with a 1:5000 dilution in PBS-tween of polyclonal sheep anti-digoxigenin Fab fragments, conjugated to alkaline phosphatase, for thirty minutes at room temperature. After washing the filters for four times fifteen minutes with PBS-tween at room temperature and once for fifteen minutes with 0.01M Tris-HCl pH 8.0, 0.15M NaCl, binding of the alkaline phosphatase to the filters was detected upon incubation with a solution of 0.33 g/l Nitroblue tetrazolium and 0.17 g/l 5-bromo-4-chloro-3-indolyl-phosphate in 0.1M Tris-HCl pH 9.6, 0.1M NaCl, 0.01M MgCl$_2$. Positive plaques were purified by two or three additional rounds of plating of isolated plaques and hybridization as described above.

Isolation of extended DNA sequences by "semi-specific" PCR

Since the initial clones isolated from the lambda gt11 library by immunological screening or from the lambda gt10 library by hybridization analysis did not contain the full-length reading frame for the respective proteins additional DNA sequences were generated by the polymerase chain reaction.

Towards this end primary cDNA libraries in lambda gt11 were amplified: 5*10$^4$ pfu were incubated with 600 μl E. coli Y1090$^-$ cells and plated. After overnight incubation the top agarose layer was collected in a tube, 5 ml of phage dilution buffer (Tris (pH 7.6) 10 mM,MgCl$_2$ 10 mM,NaCl 100 mM,gelatine 1 mg/ml) were added and incubated for 16 h at 4° C. The suspension was cleared by centrifugation and the supernatant was used directly for PCR reactions. With modifications the method of Blakely and Carman (Bio Techniques 10,53–55 (1991)) was used. To 2.5 μl of the supernatant containing about 10$^{10}$ pfu/μl, 1 μl dNTP stock solution (20 mM of each dNTP), 10 μl of buffer (containing Tris 150 mM (pH 7.6), KCl 600 mM, MgCl$_2$ 25 mM), 1 μg of each primer, 3 μl DMSO and 2.5 U of Taq Polymerase (Cetus/Perkin-Elmer) was added in a final reaction mixture of 100 μl.

One of each primer set is specific for the Eimeria sequence to be extended, i.e. for either Eam20, Eam45 or Eam100; the second primer of each set is a "general" primer, homologous to the 3'-end of the β-galactosidase gene of lambda gt11 (Lambda gt11 Primer (reverse), 24 MER #1222 (New England Biolabs).

PCR fragments were purified by gel-electrophoresis and cloned in the vector of the TA-Cloning kit (Invitrogen) exactly according to the instructions of the manufacturer. Resulting clones were sequenced. To correct for PCR-caused errors in the individual DNA clones at least three independent clones for each extended DNA fragment were sequenced.

DNA sequence analysis

The inserts from the λgt10 and λgt11 clones indicated above were subcloned into the pGEM-4Z vector (Promega) for sequencing. Sequencing reactions were carried out by the dideoxy method (Bankier & Barrell, Techniques in the Life Sciences (Biochemistry) 85: Techniques in Nucleic Acids Biochem. 1-34; 1983). Sequencing primers were synthesized on an Applied BioSystems 380B apparatus using the β-cyanoethylphosphoramadite chemistry.

B. Results

Figure 10:
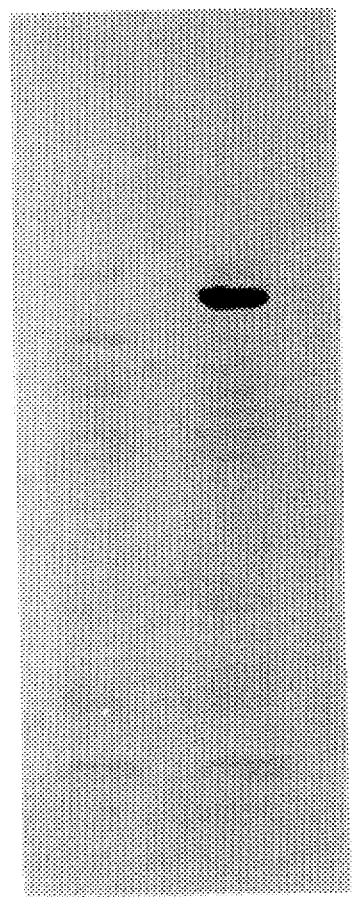
FIG. 10 is a Western blot analysis of lambda gt11/Eam200 expression product.

Clones coding for (part of) the Eam200 reading frame were isolated by using mouse monoclonal antibodies for screening a lambda gt11 cDNA library. One out of every $2.10^5$ independent clones was found to be positive. The reaction of a number of different mouse monoclonal antibodies against Eam200 such as E.ACER 12B-2A, E.ACER 12C-2B and E.ACER 12B-2B, with the clone which was selected for further analysis was considered as sufficient and conclusive evidence for the identity of the reading frame contained within this clone. The reaction of the fusion protein coded for by a lysogenic strain of lambda gt11/Eam 200 with antibody E.ACER 12B-2B is shown in FIG. 10. The sequence of part of Eam200 is shown in SEQ ID No.'s 1 and 2. As can be seen the total insert length is 1491 bp, of which 1341 bp are coding for protein.

Monospecific anti-Eam45 serum from rabbit 5706 (see Example 2) was used for the isolation of clones coding for this protein. Two clones were isolated out of $5.10^4$ plaques screened. The inserts Of these clones, which were called Eam45 M1 and Eam45 M3, were 817 and 786 bp respectively. Both inserts were expressed in E.coli: Eam45 M1 coded for a protein of about 13 kD and Eam45 M3 for a 24 kD protein. Both expression products reacted on Western blots with the monospecific rabbit anti-Eam45 serum (data not shown). In antibody-select experiments antibodies eluted from clone M3 were reactive with the merozoite-derived Eam45 protein (FIG. 9); no reaction at all was observed when such experiments were done with clone M1. Extended clones from Eam45 M1 and M3 were prepared by PCR as described in the Methods: for M1 an extended PCR fragment was found of 127 bp and for M3 845 additional bp were found. The total sequence obtained for M1 is therefore 944 bp and for M3 1631 bp. These sequences which have been called Eam45 M1E and Eam45 M3E respectively are shown in SEQ ID NO.'s 3 (M1E) and 5 (M3E). The first ATG in M1E is present at position 82 to 84 and in M3E at position 505 to 507; both ATG's are preceded by in-frame upstream stop codons and therefore most likely represent the true initiation codons. The primary amino acid sequences coded for by Eam45 M1E and M3E are given in SEQ ID NO's 4 (M1E) and 6 (M3E). Monospecific anti-Eam20 from rabbit 5796 (see Example 2) was used for the isolation of clones coding for this protein. All clones isolated from a lambda gt11 expression library had inserts smaller than 200 bp. Therefore, the insert from one of these clones was used as a probe to screen a lambda gt10 library. One out of every $2.10^5$ plaques screened was positive. The longest insert found was 579 bp and has a coding capacity of 11 kD. From this an extended clone was generated using PCR, which contained an additional 221 bp. The total sequence obtained for Eam20 is therefore 800 bp; the clone has been called Eam20E and its sequence is shown in SEQ ID NO.7.

Although the reading frame of Eam20E is completely open from the first nucleotide on, most likely the first ATG (positon 80 to 82 in SEQ ID NO.7) represents the initiation codon. The protein coding sequence of Eam20E (SEQ ID NO.8) should thus preferably be read from Met at position 27.

For the isolation of clones coding for the Eam100 protein a monospecific serum (323) was used from a chicken which had been immunised with immunoaffinity-purified Eas100. Eas100 was purified by affinity chromatography using immobilized monoclonal antibody E.ACER5F-2 and used to raise antibodies, in chickens as described in Example 2. These antibodies were used to screen a lambda gt11 cDNA library derived from E. acervulina merozoite mRNA. One clone was found to be positive of the $2.10^5$ clones screened. Antibodies selected by this clone from different sera were found to react on Western blots with a 100 kD protein present both in merozoites and sporozoites (see FIG. 8), thus demonstrating that the reading frame of this clone indeed codes for (part of) the 100 kD protein. The insert of this clone was 1259 bp long and has a coding capacity of 34 kD (data not shown). From this an extended clone was generated using PCR, which contained an additional 1116 bp. The total sequence obtained for Eam100 is therefore 2375 bp; it has been called Eam100E and is shown in SEQ ID NO.9. Its deduced amino acid sequence is shown in SEQ ID NO. 10. In this case the coding sequence may also be read from Met at position 106.

EXAMPLE 4

Immunization of Chickens with Affinity-Purified Antigens

A. Methods

Starting with $6\times10^{10}$ E.avervulina 72 hr merozoites hydrophobic and hydrophilic antigens were separated by TX114 extraction (Example 2). The individual antigens were purified by Immuno-affinity chromatography.

TABLE 1

Yield of purified E. acervulina merozoite antigens and dose used for immunization.

| Antigen | Yield in mg protein | Microgram per dose |
|---|---|---|
| Eam200 | 0.37 | 5.4 |
| Eam100 | 1.74 | 25 |
| Eam45 | 2.55 | 25 |
| Eam20 | 1.68 | 25 |

Protein concentrations were determined using the Bicinchonic acid assay (Pierce Chemicals) according to the manufacturer's prescription.

Immunization schedule

Purified antigens were mixed with Quil A (Superfos Biosector A/S) so that every dose contained 100 microgram Quil A in a total volume of 0.5 ml. Groups of 20 White Leghorn chickens were kept in isolators from day of hatch until day of priming. The chickens were immunised by three injections of 0.5 ml Quil A/antigen given subcutaneously in the neck with weekly intervals. The antigen dose is given in the Table above.

Challenge

Ten days after the third inoculation chickens were individually dosed with 200-300 freshly sporulated E. acervulina oocysts per os. Oocysts shed were counted from feces-samples taken from days 4 to 7 after infection.

Immunological parameters
Antibody titers

Serum samples were taken prior to every immunization, prior to challenge and 7 days post-challenge. Sera were tested for antibody titers against *E. acervulina* merozoite antigen using an ELISA-test. Hereto $1 \times 10^5$ merozoites in 0.1 ml of 50 mM carbonate/bicarbonate buffer pH 9,6 were coated per well of a microtiter plate by heating overnight at 50° C. Plates were washed, blocked with bovine serum albumin and incubated with different serum dilutions for 1 hr at 37° C., washed several times and subsequently incubated with peroxidase-labelled Rabbit anti-Chicken IgG(H+L) for 1 hr at 37° C. After appropriate washing the positive binding was detected using the Urea-TMB substrate and absorption was measured at 450 nm. Titers are presented as $^2$log(endpoint dilution).

Lymphocyte stimulation

Prior to challenge peripheral bloodcells were taken from 10 chickens of each group. Peripheral blood leucocytes were isolated by centrifugation of the total blood for 6 min at 64 g at ambient temperature. The buffy coat was removed and residual cells and plasma were remixed and spun again. The white cells harvested from two cycles were counted in a Haemocytometer and concentration adjusted to $1 \times 10^7$ cells per ml in RPMI 1640 (Dutch modification).

*E. acervulina* merozoites ($4 \times 10^8$) were suspended in 6,7 ml RPMI 1640 and sonicated using a microtip-equipped Branson sonifier at position 6 for 3×20 seconds with intermediate cooling. This was diluted to meet the concentration used for the stimulation. 96 well round-bottom Tissue culture plates were seeded with 0.05 ml cell suspension, 0.150 ml antigen suspension, cultured for 64 hr at 41° C. under 5% $CO_2$ atmosphere. Subsequently 0.5 microCurie $^3$-H-Thymidine was added per well and 8 hrs later the cells were harvested on a glass-fiber filter (Pharmacia/LKB) using a 96 well Cell Harvester (Skatron Norway). The filters were saturated with scintillation fluid (LKB BetaScint) and counted in a Betaplate 1205 (Pharmacia/LKB Sweden).

B. Results
Immunological parameters
Antibody titers

Table 2 shows the mean pre-challenge titers of the different groups tested in ELISA against *A. acervulina* merozoite antigen. All antigens induced high Ab-titers which differed a factor of minimum 30 from the controls.

TABLE 2

Mean pre-challenge antibody titers in ELISA against *E. acervulina* merozoites

| Group | Ab-titer $^2$Log (dilution) |
|---|---|
| Eam200 | 16.7 ± 1.1 |
| Eam100 | 14.8 ± 1.4 |
| control | 9.9 ± 1.0 |
| Eam45 | 16.1 ± 1.4 |
| Eam20 | 15.0 ± 1.6 |
| control | 10.1 ± 1.4 |

Lymphocyte stimulation

PBL of all groups were stimulated with three different concentrations of *E. acervulina* merozoite antigens i.e. $5 \times 10^5$, $1 \times 10^6$ and $3 \times 10^6$ sonicated merozoites per well respectively. For every group the optimal concentration was determined.

Table 3 shows the mean Dcpm (the cpm of the antigen-stimulated wells minus those of the non-stimulated control). It appeared that all antigens induced a positive T-cell response detectable in the peripheral blood at the time of challenge. In general 6 or 7 out of 10 birds responded versus none in the controls.

TABLE 3

Mean incorporation of $^3$H-Thymidine after stimulation with merozoite antigen of PBL from groups immunised with different purified *E. acervulina* merozoite antigens expressed as Dcpm.

| Group | $^3$H-thymidine incorporation in Dcpm | responders/ non-responders |
|---|---|---|
| Eam200 | 692 | 6/4 |
| Eam100 | 1192 | 8/2 |
| control | 14 | 1/9 |
| Eam45 | 716 | 8/2 |
| Eam20 | 922 | 9/1 |
| control | 6 | 1/9 |

Oocyst production

Table 4 shows the mean number of oocysts shedded per group as percentage of the control, which received only the Quil A adjuvant. Eam200, Eam100, Eam45 and Eam20 reduced the oocyst output.

TABLE 4

Oocyst output in percents from control

| Group | % oocysts (control output = 100%) |
|---|---|
| Eam200/Quil A | 83 |
| Eam100/Quil A | 83 |
| Eam45/Quil A | 62 |
| Eam20/Quil A | 72 |

Legends

Figure 1B:
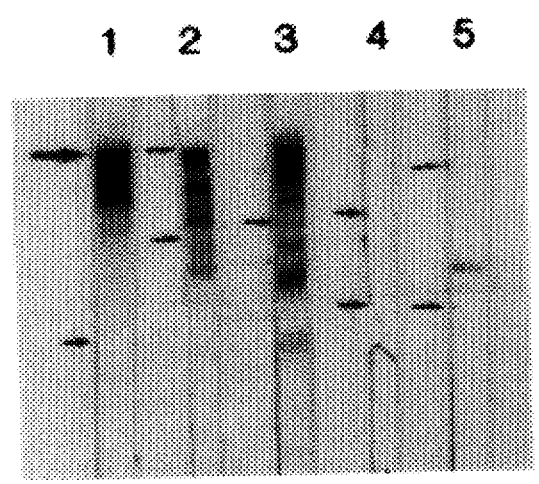

FIG. 1A & B:
Recognition of Mabs E.ACER 11A-2A (Panel A) and E.ACER 12B-2B (Panel B) on different Eimeria species and stages.
Lanes 1: *E.acervulina* merozoites; non-reduced SDS-PAGE (NR),
Lanes 2: *E.acervulina* merozoites; reduced,
Lanes 3: *E.acervulina* sporozoites; NR,
Lanes 4: *E.tenella* 2nd gen. merozoites; NR,
Lanes 5: *E.tenella* sporozoites; NR.
Arrows indicate the position of molecular weight markers: beta-galactosidase (MW=116 kD), lower arrow and myosin (MW=200 kD), upper arrow (not indicated in lanes 3).

FIG. 2A & B:
Recognition of Mabs E.ACER 10C-2A (Panel A) and E.ACER 10E-2 (Panel B) on different Eimeria species and stages.
Lanes 1: *E.acervulina* merozoites; non-reduced SDS-PAGE (NR),
Lanes 2: *E.acervulina* merozoites; reduced,
Lanes 3: *E.acervulina* sporozoites; NR,
Lanes 4: *E.tenella* 2nd gen. merozoites; NR,
Lanes 5: *E.tenella* sporozoites; NR.
Arrows indicate the position of positively recognised bands.

FIG. 3:
Western blot (non-reduced PAGE) of different fractions of TX114 extraction of *E.acervulina* merozoites. The blot was probed with a combination of Mabs recognising Eam200 (indicated as "200"), Eam100 ("100"), Eam45 ("50") and Eam20 ("20").
Lane 1: non-solubilised material (concentrated),
Lane 2: solubilised total material, Lane 3: hydrophilic fraction (waterphase),
Lane 4: sucrose fraction (interphase),
Lane 5: hydrophobic fraction (detergent phase).

FIG. 4:
Western blot (non-reduced PAGE) of different fractions of immuno-affinity purification usign E.ACER 10C-2A. The blot was probed with K8275 polyclonal rabbitserum.
Lane 2: molecular weight markers,
Lane 3: TX114 hydrophobic fraction,
Lanes 4–10: fractions from washing cycles after binding,
Lanes 11–14: acidic elution fractions (pH 2.6),
Lanes 15–18: 3M KSCN elution,
Lane 19: non-bound fraction.

FIG. 5:
Western blot (non-reduced PAGE) of different fractions of immuno-affinity purification using E.ACER 10E-2. The blot was probed with K8275 polyclonal rabbitserum.
Lane 2: molecular weight markers,
Lane 3: TX114 hydrophobic fraction after E.ACER 10C-2A column passage,
Lane 4: non-bound fraction,
Lanes 5–9: fractions from washing cycles after binding,
Lanes 10–12: acidic elution fractions (pH 2.6),
Lanes 14–18: 3M KSCN elution.

FIG. 6:
Western blot (non-reduced PAGE) of different fractions of immuno-affinity purification using E.ACER 5F-2. The blot was probed with polyclonal rabbitserum raised against E.acervulina sporozoites (K802).
Lane 1: TX114 hydrophilic fraction of sporozoites,
Lane 2: non-bound fraction,
Lanes 3–5: acidic elutions fractions (pH 2.6),
Lanes 6–7: 3M KSCN elution.
Arrow indicates the Eas100 doublet.

FIG. 7:
Western blot (non-reduced PAGE) of different fractions of-immuno-affinity purification using E.ACER 11A-2A. The blot was probed with a set of monoclonal antibodies reactive with Eam200, Eam100, Eam45 and Eam20.
Lane 1: molecular weight markers,
Lane 2: TX114 hydrophilic fraction,
Lane 3: non-bound fraction,
Lane 4: acidic elution fraction (pH 2.6).
Just above the Eam200 band a thin IgG band is visible in lanes 3 and 4, caused by leakage of Mab from the column.

Figure 8:
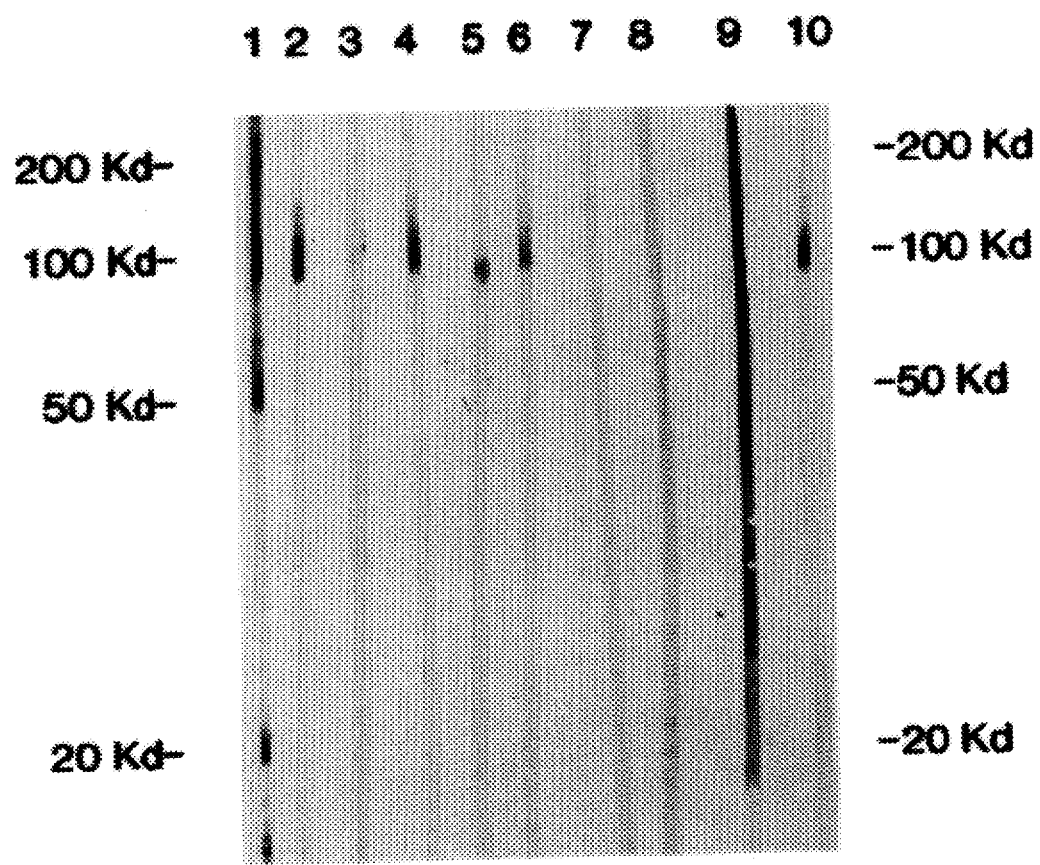
FIG. 8 depicts the reaction of clone Eam100-selected antibodies on Western blot strips of *E. acervulina* proteins.

FIG. 8:
Reaction of clone Eam100-selected antibodies on Western blot strips of E.acervulina proteins (non-reduced PAGE). Apart from strip 5 which contains sporozoite proteins from E.acervulina all the other strips contain merozoite proteins. Strips were reacted with:
1. antiserum against total proteins from E.acervulina merozoites (from rabbit K8275)
2. monospecific antiserum against immuno-affinity purified Eam100 (from chicken 323)
3. antibodies selected by clone lambda gt11/Eam100 from chicken 323 antiserum
4. antibodies selected by clone lambda gt11/Eam100 from rabbit K8275 antiserum
5. antibodies selected by clone lambda gt11/Eam100 from rabbit K802 antiserum
6. same as 5
7. antibodies selected by wild type lambda gt11 from chicken 323 antiserum
8. antibodies selected by wild type lambda gt11 from rabbit K802 antiserum
9. antibodies against total sporozoite proteins (from rabbit K802)
10. monoclonal antibody E.ACER 5F-2.

FIG. 9:
Reaction of clone Eam45 (M3)-selected antibodies on Western blot strips of E.acervulina proteins (non-reduced PAGE).
All strips contain merozoite proteins. They were reacted with:
1. antibodies selected by clone lambda gt11/Eam45 (M3) from rabbit K5706 antiserum
2. antibodies selected by clone lambda gt11/Eam45 (M3) from rabbit K5794 antiserum
3. antibodies selected by clone lambda gt11/Eam45 (M3) from rabbit K5796 antiserum
4. antibodies selected by clone lambda gt11/Eam45 (M3) from rabbit K8275 antiserum
5. monospecific antiserum against immuno-affinity purified Eam45 (from rabbit K5706)
6. antiserum against the TX114 hydrophobic extract from merozoites (from rabbit K5794)
7. monospecific antiserum against immuno-affinity purified Eam45 (from rabbit K5792)
8. antibodies selected by wild type lambda gt11 from rabbit K5706 antiserum
9. antibodies selected by wild type lambda gt11 from rabbit K5794 antiserum
10. antibodies selected by wild type lambda gt11 from rabbit K5796 antiserum
11. antibodies selected by wild type lambda gt11 from rabbit K8275 antiserum
12. monoclonal antibody E.ACER 10C-2A.

FIG. 10
Western blot analysis of lambda gt11/Eam200 expression product.
Expression products from a lysogenic strain of lambda gt11/Eam200 were run (reduced) on a SDS-PAGE gel, blotted and probed with monoclonal antibody E.ACER 12B-2B (lane 2). As a control lambda gt11 expression products were run in lane 1.

We claim:

1. A DNA molecule comprising a nucleic acid sequence coding for an Eimeria polypeptide having the amino acid sequence of SEQ ID NO:10, or a fragment of said polypeptide that specifically binds with antibody raised to said polypeptide, wherein the DNA molecule is free from other genetic material of Eimeria.

2. The DNA molecule of claim 1, wherein the nucleic acid sequence has the DNA sequence shown in SEQ ID NO:9, or a part of said DNA sequence that codes for said fragment of said polypeptide.

3. A recombinant vector molecule comprising a nucleic acid sequence according to claim 1.

4. A recombinant vector molecule according to claim 3, wherein the nucleic acid sequence is operably linked to expression control sequences.

5. A recombinant vector molecule comprising a nucleic acid sequence according to claim 2.

6. A recombinant vector molecule according to claim 5, wherein the nucleic acid sequence is operably linked to expression control sequences.

7. A recombinant vector virus harboring a heterologous nucleic acid sequence, wherein said sequence is the nucleic acid sequence according to claim 1.

8. The recombinant vector virus according to claim 7, wherein said sequence is the nucleic acid sequence according to claim 2.

9. A host cell transfected with a nucleic acid sequence according to claim 1.

10. A host cell transfected with a nucleic acid sequence according to claim 2.

11. A host cell transfected with a recombinant vector molecule according to claim 3.

12. A host cell transfected with a recombinant vector molecule according to claim 4.

13. A host cell transfected with a recombinant vector molecule according to claim 5.

14. A host cell transfected with a recombinant vector molecule according to claim 6.

15. A host cell transfected with a recombinant vector virus according to claim 7.

16. A host cell transfected with a recombinant vector virus according to claim 8.

* * * * *